(12) United States Patent
Uhrich et al.

(10) Patent No.: US 9,630,905 B2
(45) Date of Patent: Apr. 25, 2017

(54) AMPHIPHILIC MACROMOLECULES AND METHODS OF USE THEREOF

(71) Applicant: Rutgers, The State University of New Jersey, New Brunswick, NJ (US)

(72) Inventors: Kathryn E. Uhrich, New Brunswick, NJ (US); Prabhas Moghe, New Brunswick, NJ (US); Dalia Abdelhamid, Minia (EG); Li Gu, New Brunswick, NJ (US); Yingyue Zhang, New Brunswick, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 14/847,986

(22) Filed: Sep. 8, 2015

(65) Prior Publication Data

US 2016/0068467 A1  Mar. 10, 2016

Related U.S. Application Data

(60) Provisional application No. 62/047,449, filed on Sep. 8, 2014.

(51) Int. Cl.
  *C07C 69/708* (2006.01)
  *C08G 65/332* (2006.01)

(52) U.S. Cl.
  CPC ........ *C07C 69/708* (2013.01); *C08G 65/3322* (2013.01)

(58) Field of Classification Search
  CPC .......................... C07C 69/708; C08G 65/3322
  See application file for complete search history.

(56) References Cited

U.S. PATENT DOCUMENTS

| | | | |
|---|---|---|---|
| 4,065,598 A | 12/1977 | Takahashi et al. | |
| 4,938,949 A | 7/1990 | Borch et al. | |
| 6,328,988 B1 | 12/2001 | Uhrich et al. | |
| 6,365,146 B1 | 4/2002 | Uhrich et al. | |
| 6,497,895 B2 | 12/2002 | Uhrich et al. | |
| 7,262,221 B2 | 8/2007 | Uhrich et al. | |
| 7,470,802 B2 | 12/2008 | Uhrich et al. | |
| 8,192,754 B2 | 6/2012 | Uhrich et al. | |
| 8,846,850 B2 | 9/2014 | Uhrich et al. | |
| 9,434,681 B2 | 9/2016 | Uhrich et al. | |
| 2003/0170202 A1 | 9/2003 | Uhrich | |
| 2004/0198641 A1 | 10/2004 | Uhrich et al. | |
| 2005/0089504 A1 | 4/2005 | Uhrich | |
| 2008/0057026 A1 | 3/2008 | Uhrich et al. | |
| 2009/0175932 A1 | 7/2009 | Uhrich et al. | |
| 2011/0008396 A1 | 1/2011 | Moghe et al. | |
| 2011/0229416 A1 | 9/2011 | Uhrich et al. | |
| 2012/0022159 A1 | 1/2012 | Uhrich et al. | |
| 2012/0039983 A1 | 2/2012 | Uhrich et al. | |
| 2012/0219598 A1 | 8/2012 | Uhrich et al. | |
| 2012/0225926 A1 | 9/2012 | Uhrich et al. | |
| 2014/0120057 A1 | 5/2014 | Uhrich et al. | |
| 2015/0175528 A1 | 6/2015 | Uhrich et al. | |

FOREIGN PATENT DOCUMENTS

| | | |
|---|---|---|
| JP | 06145341 | 5/1994 |
| WO | 0065024 A2 | 11/2000 |
| WO | 0105873 A1 | 1/2001 |
| WO | 03005959 A2 | 1/2003 |
| WO | 03047518 A2 | 6/2003 |
| WO | 030103594 | 12/2003 |
| WO | 2005074887 | 8/2005 |
| WO | 2009039505 A1 | 3/2009 |
| WO | 2013188882 | 12/2013 |
| WO | 2015195563 | 12/2015 |

OTHER PUBLICATIONS

Database CAPLUS in STN, Acc. No. 1948:8674, Snyder et al., Journal of the American Chemical Society (1947), 69, pp. 2672-2674 (abstract).*

Needham, et al., "Drug targeting to monocytes and macrophages using esterase-sensitive chemical motifs", J. Pharmacol. Exp. Ther. 339 (1), 132-142 (2011).

Papisov, et al., "Modeling in vivo transfer of long-circulating polymers (two classes of long circulating polymers and factors affecting their transfer in vivo)", Advanced Drug Delivery Reviews, vol. 16, pp. 127-139, 1995.

Petit, et al., "Interactions of hydrophobically modified poly(sodium acrylate) with globular proteins", Colloid Polym Sci 273, 777-781 (1995).

Plourde, et al., "Structure—Activity relations of Nanolipoblockers with the Atherogenic Domain of Human Macrophage Scavenger Receptor A", Biomacromolecules 10, 1381-1391 (2009).

Podrez, et al., "Macrophage scavenger receptor CD36 is the major receptor for LDL modified by monocyte-generated reactive nitrogen species", J. Clin Invest 105 (8), 1095-1108 (2000).

Porcar, et al., "Association between Protein Particles and Long Amphiphilic Polymers: Effect of the Polymer Hydrophobicity on Binding isotherms", Macromolecules 32 (12), 3922-3929 (1999).

Poree, et al., "Nanoscale Amphiphilic Macromolecules with Variable Lipophilicity and Stereochemistry Modulate Inhibition of Oxidized Low-Density Lipoprotein Uptake", Biomacromolecules 14 (8), 2463-2469 (2013).

Reeve, et al., "Polylactide stereochemistry: effect on enzymic degradability", Macromolecules 27 (3), 825-831 (1994).

(Continued)

*Primary Examiner* — Brian J Davis
(74) *Attorney, Agent, or Firm* — Viksnins Harris & Padys PLLP

(57) ABSTRACT

Certain embodiments of the invention provide a compound of formula (I):

$$A\text{-}X\text{—}Y\text{—}Z\text{—}R_1 \qquad (I),$$

or a salt thereof, wherein A, X, Y, Z and $R_1$ have any of the values defined in the specification, and methods of use thereof. For example, certain embodiments of the invention provide a method for inhibiting atherosclerosis or atherosclerotic development in a mammal, comprising administering to the mammal an effective amount of a compound of formula (I), or a pharmaceutically acceptable salt thereof.

20 Claims, 8 Drawing Sheets

(56) References Cited

OTHER PUBLICATIONS

Rousselle, et al., "New advances in the transport of doxorubicin through the blood-brain barrier by a peptide vector-mediated strategy", Molecular Pharmacology, Vo. 57, pp. 679-686, 2000.
Schmalenberg, et al., "Cytotoxicity of a unimolecular polymeric micelle and its degradation products", Biomacromolecules 2, pp. 851-855, 2001.
Sparks, et al., "Efficient intracellular siRNA delivery by ethyleneimine-modified amphiphilic macromolecules", Macromol Biosci 11 (9), 1192-1200 (2011).
Steinberg, et al., "Low density lipoprotein oxidation and its pathobiological significance", Journal of Biological chemistry vol. 272 (34), 20963-20966 (1997).
Sun, et al., "Functional biointerface materials inspired from nature", Chem Soc Rev 40 (5), 2909-2921 (2011).
Sun, et al., "Stereospecific interaction between immune cells and chiral surfaces", J. Am. Chem. Soc. 129 (6), 1496-1497 (2007).
Tao, et al., "Novel amphiphilic macromolecules and their in vitro characterization as stabilized micellar drug delivery systems", J. Colloid Interface Sci 298 (1), 102-110 (2006).
Temsamani, et al., "Brain drug delivery technologies: novel approaches for transporting therapeutics", PSTT, vol. 3, No. 5, pp. 155-162, 2000.
Tian, et al., "Amphiphilic scorpion-like macromolecules: design, synthesis and characterization", Macromolecules, 37, pp. 538-543, 2004.
Tian, et al., "Design and synthesis of amphiphilic poly(ethylene glycol) derivaties as a micellar drug delivery system", Polymer Preprints, 43(2), 719-720 (2002).
Tian, et al., "Design and synthesis of amphiphilic poly(ethylene glycol) derivatives as a micellar drug delivery system", Abstracts of Papers, Part 2, 224, (1-2), abstract 748, 224th ACS National Meeting (2002).
Tian, et al., "Novel amphiphilic macromolecules for drug delivery applications: design, synthesis and characterization", in Dissertation, New Brunswick, New Jersey, pp. 13-48, 114-138 and 160-175, 2004.
Torchilin, et al., "Structure and design of polymeric surfactant-based drug delivery systems", J Control Release 73 (2-3):137-72 (2001).
Tuzar, et al., "Micelles of Block and Graft Copolymers in Solutions", Surface and Colloid Science, vol. 15, pp. 1-83, 1993.
Wang, et al., "Chiral Design for Polymeric Biointerface: The Influence of Surface Chirality on Protein Adsorption", Advanced Functional Materials, vol. 21 (17), 3276-3281 (2011).
Wang, et al., "Comparison of PEG chain length and density on amphiphilic macromolecular nanocarriers: Self-assembled and unimolecular micelles", Acta Biomaterialia, 5, pp. 883-892, 2009.
Wang, et al., "Nanoscale amphiphilic macromolecules as lipoprotein inhibitors: the role of charge and architecture", Int. J. Nanomedicine, 2(4), pp. 697-705, 2007.
Wang, et al., "Stereochemistry triggered differential cell behaviours on chiral polymer surfaces", Soft Matter 6, 3851-3855 (2010).
Williams, et al., "The response-to-retention hypothesis of early atherogenesis", Arteriosclerosis, Thrombosis & Vascular Biology, vol. 15, No. 5, pp. 551-561, 1995.
York, et al., "Kinetically assembled nanoparticles of bioactive macromolecules exhibit enhanced stability and cell-targeted biological efficacy", Adv Mater 24 (6), 733-739 (2012).
Yoshiizumi, et al., "2,4-Bis(octadecanoylamino)benzenesulfonic acid sodium salt as a novel scavenger receptor inhibitor with low molecular weight", Bioorg Med Chem Lett, 14 (11), 2791-2795 (2004).
Yoshimoto, et al., "Growth stimulation and epidermal growth factor receptor induction in cyclooxygenase—overexpressing human colon carcinoma cells", Adv Exp Med Biol, 403-407 (2002).
Zeng, et al., "A polymeric micelle system with a hydrolysable segment for drug delivery", J. Biomater Sci Polym Ed. 17 (5), 591-604 (2006).
Zhang, et al., "Chiral biointerface materials", Chem Soc Rev 41 (5), 1972-1984 (2012).
Zhu, et al. "Super Microcapsules" (SMC. I. Preparation and Characterization of Star Polyethylene Oxide (POE)—Polylactide (PLA) Copolymers, J. Polym. Sci. Polm. Chem., vol. 27, p. 2151, 1989.
Abdelhamid, et al., "Design and synthesis of novel amphiphilic macromolecules for cardiovascular applications", American Chemical Society 246th National Meeting, Indianapolis, IN, Abstract 189, 1 page (Jun. 24, 2013).
Abdelhamid, et al., "Design and Synthesis of Novel Amphiphilic Macromolecules for Cardiovascular Applications", American Chemical Society 246th National Meeting, Indianapolis, IN, Poster, 4 pages (Sep. 10, 2013).
Abdelhamid, et al., "Role of Branching of Hydrophilic Domain on Physicochemical Properties of Amphiphilic Macromolecules", Polymer Chemistry 5 (4), 1457-1462 (2014).
Abdelhamid, et al., "Tartaric acid-based amphiphilic macromolecules with ether linkages exhibit enhanced repression of oxidized low density lipoprotein uptake", Biomaterials 53, 32-39 (2015).
Allen, et al., "Nano-engineering block copolymer aggregates for drug delivery", Colloids and Surfaces B: Biointerfaces 16:3-27 (1999).
Astafieva, et al., "Critical micellization phenomena in block polyelectrolyte solutions", Macromolecules 26 (26), 7339-7352 (1993).
Boullier, et al., "Phosphocholine as a pattern recognition ligand for CD36", Journal of Lipid Research, vol. 46, 969-976 (2005).
Brown, et al., "Lipoprotein metabolism in the macrophage: implications for cholesterol deposition in atherosclerosis", Annu Rev Biochem 52, 223-261 (1983).
Broz, et al., "Cell targeting by a generic receptor-targeted polymer nanocontainer platform", J Control Release 102 (2), 475-488 (2005).
Camejo, et al., "The extracellular matrix on atherogenesis and diabetes-associated vascular disease", Atherosclerosis Supplements, vol. 3, pp. 3-9, 2002.
Cammas, et al., "Functional poly[(ethylene oxide)—co-(-benzyl-L-aspartate)] polymeric micelles: block copolymer synthesis and micelles formation", Macromol. Chem. Phys., 196, pp. 1899-1905, 1995.
Chambers, et al., "Model for Aqueous Solvation Based on Class IV Atomic Charges and First Solvation Shell Effects", J. Phys. Chem. 100, 16385-16398 (1996).
Chemical Abstract, of, JP-6305820, 1994.
Chnari, et al., "Engineered polymeric nanoparticles for receptor-targeted blockage of oxidized low density lipoprotein uptake and atherogenesis in macrophages", Biomacromolecules 7(6), 1796-1805 (2006).
Chnari, et al., "Nanoscale anionic macromolecules can inhibit cellular uptake of differentially oxidized LDL", Biomacromolecules 7 (2), 597-603 (2006).
Chnari, et al., "Nanoscale anionic macromolecules for selective retention of low-density lipoproteins", Biomaterials 26 (17), 3749-3758 (2005).
De Winther, et al., "Macrophage scavenger receptor class A: A multifunctional receptor in atherosclerosis", Arterioscler Thromb Vase Biol., 20(2), 290-297 (2000).
Djodjevic, et al., "Polymeric Micelles Based on Amphiphilic Scorpion-like Macromolecules: Novel Carriers for Water-Insoluble Drugs", Pharmaceutical Research, 22(1), pp. 24-32, 2005.
Djordjevic, et al., "Amphiphilic Scorpion-like Macromolecules as Micellar Nanocarriers", Journal of Bioactive and Compatible Polymers, vol. 23 (6), 532-551 (2008).
Djordjevic, et al., "Amphiphilic Star-Like Macromolecules as Novel Carriers for Topical Delivery of Nonsteroidal Anti-Inflammatory Drugs", AAPS PharmSci, 5 (4), pp. 1-12, 2003.
Faig et al., "Amphiphilic Macromolecules with Novel Hydrophobic Chain Architectures for Atherosclerotic Applications", American Chemical Society 246th National Meeting, Indianapolis, IN, Abstract 173, 1 page (Jun. 24, 2013).
Faig, et al., "Amphiphilic Macromolecules with Novel Hydrophobic Chain Architectures for Atherosclerotic Applications", Ameri-

(56) References Cited

OTHER PUBLICATIONS can Chemical Society 246th National Meeting, Indianapolis, IN, Poster, 7 pages (Sep. 9-10, 2013).

Faig, et al., "Impact of Hydrophobic Chain Composition on Amphiphilic 2 Macromolecule Antiatherogenic Bioactivity", Biomacromolecules 15 (9), 3328-3337 (2014).

Fukami, et al., "The emerging role of human esterases", Drug Metab. Pharmacokinet 27 (5), 466-477 (2012).

Gao, et al., "A model of micellization for block copolymers in solutions", Macromolecules, vol. 26, pp. 7353-7360, 1993.

Gao, et al., "Binding of proteins to copolymers of varying hydrophobicity", Biopolymers 49 (2), 185-193 (1999).

Gitsov, et al., "Micelles with highly branched nanoporous interior: solution properties and binding capabilities of amphiphilic copolymers with linear dendritic architecture", Journal of Polymer Science: Part A: Polymer Chemistry, vol. 38, pp. 2711-2727, 2000.

Goldstein, et al., "Binding site on macrophages that mediates uptake and degradation of acetylated low density lipoprotein, producing massive cholesterol deposition", Proc Natl Acad Sci 76 (1), 333-337 (1979).

Guaderrama-Diaz, et al., "Control of scavenger receptor-mediated endocytosis by novel ligands of different length", Mol Cell Biochem 271 (1-2), 123-132 (2005).

Halgren, "Merck molecular force field. I. Basis, form, scope, parameterization, and performance of MMFF94", J. Comp. Chem, 17 (5-6), 490-519 (1996).

Harmon, et al., "In Vitro Evaluation of Amphiphilic Macromolecular Nanocarriers for Systemic Drug Delivery", Journal of Bioactive and Compatible Polymers, 24, pp. 185-197, 2009.

Hehir, et al , "Carbohydrate composition of amphiphilic macromolecules influences physicochemical properties and binding to atherogenic scavenger receptor A", Acta Biomater 8 (11), 3956-3962 (2012).

Hosokawa, et al., "Interindividual variation in carboxylesterase levels in human liver microsomes", Drug Metab. Dispos. 23 (10), 1022-1027 (1995).

Ihre, et al., "Fast and Convenient Divergent Synthesis of Aliphatic Ester Dendrimers by Anhydride Coupling", J. Am. Chem. Soc. 123 (25), 5908-5917 (2001).

Iverson, et al., "Controllable inhibition of cellular uptake of oxidized low-density lipoprotein: Structure-function relationships for nanoscale amphiphilic polymers", Acta Biomaterialia 6, 3081-3091 (2010).

Iverson, et al., "Dual use of amphiphilic macromolecules as cholesterol efflux triggers and inhibitors of macrophage athero-inflammation", Biomaterials 32, 8319-8327 (2011).

Kalyanasundaram, et al., "Environmental effects on vibronic band intensities in pyrene monomer fluorescence and their application in studies of micellar systems", J. Am. Chem. Soc. 99 (7), 2039-2044 (1977).

Kataoka, et al., "Block copolymer micelles for drug delivery: design, characterization and biological significance", Adv Drug Deilv Rev. 47(1):113-31 (2001).

Kreig, et al., "Micelle formation of randomly grafted copolymers in slightly selective solvents", Journal of Chemical Physics, vol. 115, No. 13, pp. 6243-6251, 2001.

Laizure, et al., "The Role of Human Carboxylesterases in Drug Metabolism: Have We Overlooked Their Importance?", Pharmacotherapy: The Journal of Human Pharmacology and Drug Therapy, 33 (2), 210-222 (2013).

Langer, et al., "New methods of drug delivery", Science, 249, pp. 1527-1533, 1990.

Lewis, et al., "In silico design of anti-atherogenic biomaterials", Biomaterials 34 (32), 7950-7959 (2013).

Li, et al. "The macrophage foam cell as a target for therapeutic intervention", Nature Medicine 8 (11), 1235-1242 (2002).

Liu, et al. "Unimolecular micelles: Synthesis and characterization of amphiphilic polymer systems", Journal of Polymer Science, Part A:P Polymer Chemistry, 37(6), 703-711 (1999).

Lloyd-Jones, et al., "Heart disease and stroke statistics—2010 update: a report from the American Heart Association", Circulation 121 (7), e46-e215 (2010).

Makino, et al., "Control of in vivo blood clearance time of polymeric micelle by stereochemistry of amphiphilic polydepsipeptides", J. Control Release 161 (3), 821-825 (2012).

Meng, et al., "Mesomorphic behavior and optical properties of liquid-crystalline polysiloxanes bearing different chiral groups", Journal of Applied Polymer Science, vol. 114 (4), 2195-2203 (2009).

Moghimi, et al., "Exploiting bone marrow microvascular structure for drug delivery and future therapies", Advanced Drug Delivery Reviews, vol. 17, pp. 61-73, 1995.

Moghimi, et al., "Long-circulating and target-specific nanoparticles: theory to practice", J. Pharm. Rev. vol. 53(2), pp. 283-318, 2001.

Moore, et al., "Room temperature polyesterification", Macromolecules 23 (1), 65-70 (1990).

* cited by examiner

Conventional AM

Ether-branched AM

Amine-branched AM

Amide-branched AM

Hydrocarbon-branched AM

FIG. 7A : M12P5

FIG. 7B : T12P5-meso

FIG. 7C : T(12-O)P5

AMPHIPHILIC MACROMOLECULES AND METHODS OF USE THEREOF

CROSS-REFERENCE TO RELATED APPLICATION(S)

This patent application claims the benefit of priority of U.S. application Ser. No. 62/047,449, filed Sep. 8, 2014, which application is herein incorporated by reference.

GOVERNMENT FUNDING

This invention was made with government support under R01 HL107913 awarded by the National Institutes of Health. The government has certain rights in the invention.

BACKGROUND

Cardiovascular diseases are the leading cause of mortality in developed countries. Atherosclerosis, defined as the buildup of lipid rich plaques within the vascular intima, is the foremost pathology underlying these conditions. This process initiates with accumulation of oxidized low density lipoproteins (oxLDL) within the vessel walls, triggering monocyte recruitment, diapedesis and differentiation to macrophages, which subsequently uptake oxLDL via scavenger receptors. This unregulated uptake of oxLDL leads to formation of foam cells and secretion of inflammatory mediators (Yoshimoto et al., *Advances in experimental medicine and biology* 2002, 507, 403-7). The atherogenic accumulation of lipid laden macrophages results in plaques that can exhibit the clinical endpoints of myocardial infarction, stroke or peripheral arterial disease. Traditional therapies to reduce vascular lipid burden focus on lowering the hepatic synthesis of cholesterol, however, these therapies fail to target lesion development.

Accordingly, new agents and methods for treating atherosclerosis are needed.

SUMMARY OF THE INVENTION

Certain embodiments of the invention provide a compound of formula (I):

$$A-X-Y-Z-R_1 \qquad (I),$$

or a salt thereof, wherein:

A is a carboxy group or is absent;

X is a straight chain or branched chain aliphatic group containing from 2 carbons to about 10 carbons, wherein the aliphatic group is substituted with 1 or more groups independently selected from $-OR^a$, $-NR^bR^c$, $-NR^bC(=O)R^d$, and $-R^e$; wherein $R^a$ is independently selected from a $-(C_1-C_{20})$alkyl, $-(C_2-C_{20})$alkenyl and $-(C_2-C_{20})$alkynyl; wherein $R^b$ is independently H or $(C_1-C_6)$alkyl; wherein $R^c$ is independently selected from a $-(C_1-C_{20})$alkyl, $-(C_2-C_{20})$alkenyl and $-(C_2-C_{20})$alkynyl; wherein $R^d$ is independently selected from a $-(C_1-C_{20})$alkyl, $-(C_2-C_{20})$alkenyl and $-(C_2-C_{20})$alkynyl; and wherein $R^e$ is independently selected from a $-(C_1-C_{20})$alkyl, $-(C_2-C_{20})$alkenyl and $-(C_2-C_{20})$alkynyl;

Y is $-C(=O)-$, $-C(=S)-$, or is absent;

Z is O, S or NH; and $R_1$ is a polyether.

Certain embodiments of the invention provide a composition comprising a plurality of compounds of formula (I) as described herein in a solvent.

Certain embodiments of the invention provide an aggregate structure comprising a plurality of compounds of formula (I), as described herein, and a solvent.

Certain embodiments of the invention provide a method for preparing an aggregate structure, comprising combining a plurality of compounds of formula (I), as described herein, in a solvent; and allowing them to form the aggregate structure.

Certain embodiments of the invention provide aggregate formed by the method described herein.

Certain embodiments of the invention provide an encapsulate comprising a molecule surrounded or partially surrounded by a plurality of compounds of formula (I), as described herein.

Certain embodiments of the invention provide a method for preparing an encapsulate, comprising combining a) a plurality of compounds of formula (I), as described herein; b) a molecule; and c) a solvent; and allowing the compounds of formula (I) to aggregate around the molecule, to provide the encapsulate.

Certain embodiments of the invention provide a pharmaceutical composition comprising a compound of formula (I), as described herein, or a pharmaceutically acceptable salt thereof, and a pharmaceutically acceptable carrier.

Certain embodiments of the invention provide a pharmaceutical composition comprising an encapsulate, as described herein, and a pharmaceutically acceptable carrier.

Certain embodiments of the invention provide a method for inhibiting oxLDL uptake by a cell, comprising contacting the cell in vitro or in vivo with a compound of formula (I), as described herein, or a pharmaceutically acceptable salt thereof, or an encapsulate as described herein.

Certain embodiments of the invention provide a method of preventing foam cell formation in a mammal, comprising administering to the mammal an effective amount of a compound of formula (I), as described herein, or a pharmaceutically acceptable salt thereof, or an encapsulate, as described herein.

Certain embodiments of the invention provide a method for inhibiting atherosclerosis or atherosclerotic development in a mammal, comprising administering to the mammal an effective amount of a compound of formula (I), as described herein, or a pharmaceutically acceptable salt thereof, or an encapsulate as described herein.

Certain embodiments of the invention provide a compound of formula (I), as described herein, or a pharmaceutically acceptable salt thereof, or an encapsulate, as described herein, for the prophylactic or therapeutic treatment of atherosclerosis.

Certain embodiments of the invention provide a compound of formula (I), as described herein, or a pharmaceutically acceptable salt thereof, or an encapsulate, as described herein, for use in medical treatment.

Certain embodiments of the invention provide the use of a compound of formula (I), as described herein, or a pharmaceutically acceptable salt thereof, or an encapsulate, as described herein, for the preparation of a medicament for inhibiting atherosclerosis or atherosclerotic development in a mammal.

The invention also provides processes and intermediates disclosed herein that are useful for preparing a compound of formula I or a salt thereof. For Example, the intermediates of formulae 3a, 3b, 3c, 4a, 4b, 4c, 6a, 6b, and 6c represent embodiments of the invention.

DETAILED DESCRIPTION

Figure 1:
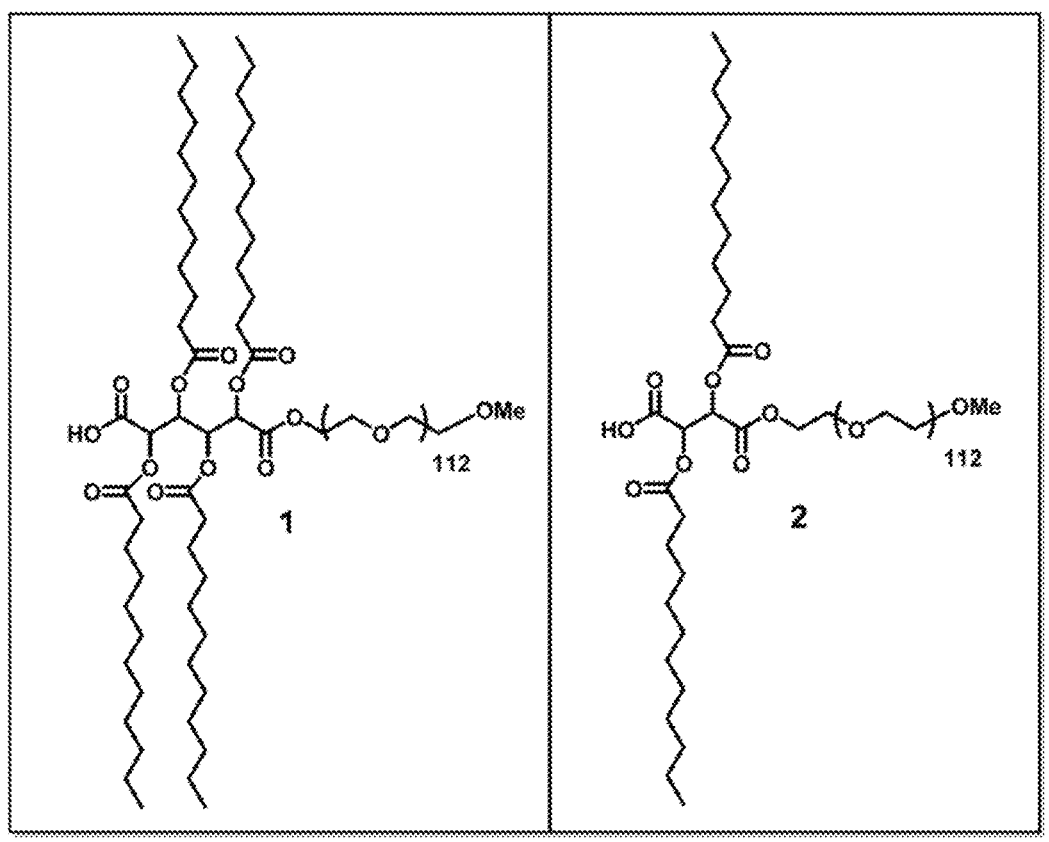
FIG. 1. Chemical structure of ester-based AMs based on mucic acid (1) and tartaric acid (2).

Certain embodiments of the invention provide a compound of formula (I):

A-X—Y—Z—R₁   (I), or a salt thereof, wherein:

A is a carboxy group or is absent;

X is a straight chain or branched chain aliphatic group containing from 2 carbons to about 10 carbons, wherein the aliphatic group is substituted with 1 or more groups independently selected from $-OR^a$, $-NR^bR^c$, $-NR^bC(=O)R^d$, and $-R^e$; wherein $R^a$ is independently selected from a $-(C_1-C_{20})$alkyl, $-(C_2-C_{20})$alkenyl and $-(C_2-C_{20})$alkynyl; wherein $R^b$ is independently H or $(C_1-C_6)$alkyl; wherein $R^c$ is independently selected from a $-(C_1-C_{20})$alkyl, $-(C_2-C_{20})$alkenyl and $-(C_2-C_{20})$alkynyl; wherein $R^d$ is independently selected from a $-(C_1-C_{20})$alkyl, $-(C_2-C_{20})$alkenyl and $-(C_2-C_{20})$alkynyl; and wherein $R^e$ is independently selected from a $-(C_1-C_{20})$alkyl, $-(C_2-C_{20})$alkenyl and $-(C_2-C_{20})$alkynyl;

Y is $-C(=O)-$, $-C(=S)-$, or is absent;

Z is O, S or NH; and

R₁ is a polyether.

The Variable "A"

As described herein A is a carboxy group or is absent. In certain embodiments, A is absent. In certain embodiments, A is a carboxy group.

The Variable "X"

As described herein, X is a straight chain or branched chain aliphatic group containing from 2 carbons to about 10 carbons (e.g., 2, 3, 4, 5, 6, 7, 8, 9 or 10 carbons), wherein the aliphatic group is substituted with 1 or more groups (e.g., 1, 2, 3, 4, 5, 6, 7, 8, 9, 10 or more groups) independently selected from $-OR^a$, $NR^bR^c$, $-NR^bC(=O)R^d$, and $R^e$; wherein $R^a$ is independently selected from a $-(C_1-C_{20})$alkyl, $-(C_2-C_{20})$alkenyl and $-(C_2-C_{20})$alkynyl; wherein $R^b$ is independently H or $(C_1-C_6)$alkyl; wherein $R^c$ is independently selected from a $-(C_1-C_{20})$alkyl, $-(C_2-C_{20})$alkenyl and $-(C_2-C_{20})$alkynyl; wherein $R^d$ is independently selected from a $-(C_1-C_{20})$alkyl, $-(C_2-C_{20})$alkenyl and $-(C_2-C_{20})$alkynyl; and wherein $R^e$ is independently selected from a $-(C_1-C_{20})$alkyl, $-(C_2-C_{20})$alkenyl and $-(C_2-C_{20})$alkynyl.

As used herein, the term "aliphatic group" includes linear chain hydrocarbon compounds that are saturated or unsaturated or branched chain hydrocarbon compounds that are saturated or unsaturated. The unsaturated hydrocarbon aliphatic groups include one or more carbon-carbon double bonds or carbon-carbon triple bonds or any combination of double or triple bonds.

The straight chain or branched chain aliphatic group typically contains from between 2 carbons to about 10 carbons, e.g., from about 2 to about 6 carbons, e.g., from about 2 to about 4 carbons, e.g., 2 carbons. In certain embodiments, straight chain or branched chain aliphatic group is ethylene. In certain embodiments, straight chain or branched chain aliphatic group is $-CH_2CH_2-$. Additionally, the aliphatic group is substituted with 1 or more groups, e.g., 1 to 10 groups, e.g., 1 to 6 groups, e.g., 1 to 4 groups, e.g., 2 to 4 groups, or e.g., 2 groups, independently selected from $-OR^a$, $-NR^bR^c$, $-NR^bC(=O)R^d$, and $-R^e$.

In certain embodiments, the aliphatic group is substituted with 1 or more $-OR^a$ groups. In certain embodiments, $R^a$ is $-(C_1-C_{20})$alkyl, e.g., $-(C_6-C_{14})$alkyl or $-(C_8-C_{12})$alkyl. In certain embodiments, $R^a$ is $-(C_2-C_{20})$alkenyl, e.g., $-(C_6-C_{14})$alkenyl or $-(C_8-C_{12})$alkenyl. In certain embodiments, $R^a$ is $-(C_2-C_{20})$alkynyl, e.g., $-(C_6-C_{14})$alkynyl or $-(C_8-C_{12})$alkynyl.

In certain embodiments, the aliphatic group is substituted with 1 or more $-NR^bR^c$ groups. In certain embodiments, $R^b$ is H. In certain embodiments, $R^b$ is $(C_1-C_6)$alkyl. In certain embodiments, $R^c$ is $-(C_1-C_{20})$alkyl, e.g., $-(C_6-C_{14})$alkyl or $-(C_8-C_{12})$alkyl. In certain embodiments, $R^c$ is $-(C_2-C_{20})$alkenyl, e.g., $-(C_6-C_{14})$alkenyl or $-(C_8-C_{12})$alkenyl. In certain embodiments, $R^c$ is $-(C_2-C_{20})$alkynyl, e.g., $-(C_6-C_{14})$alkynyl or $-(C_8-C_{12})$alkynyl.

In certain embodiments, the aliphatic group is substituted with 1 or more $-NR^bC(=O)R^d$ groups. In certain embodiments, $R^b$ is H. In certain embodiments, $R^b$ is $(C_1-C_6)$alkyl. In certain embodiments, $R^d$ is $-(C_1-C_{20})$alkyl, e.g., $-(C_6-C_{14})$alkyl or $-(C_8-C_{12})$alkyl. In certain embodiments, $R^d$ is $-(C_2-C_{20})$alkenyl, e.g., $-(C_6-C_{14})$alkenyl or $-(C_8-C_{12})$alkenyl. In certain embodiments, $R^d$ is $-(C_2-C_{20})$alkynyl, e.g., $-(C_6-C_{14})$alkynyl or $-(C_8-C_{12})$alkynyl.

In certain embodiments, the aliphatic group is substituted with 1 or more $-R^e$ groups. In certain embodiments, $R^e$ is $-(C_1-C_{20})$alkyl, e.g., $-(C_6-C_{14})$alkyl or $-(C_8-C_{12})$alkyl. In certain embodiments, $R^e$ is $-(C_2-C_{20})$alkenyl, e.g., $-(C_6-C_{14})$alkenyl or $-(C_8-C_{12})$alkenyl. In certain embodiments, $R^e$ is $-(C_2-C_{20})$alkynyl, e.g., $-(C_6-C_{14})$alkynyl or $-(C_8-C_{12})$alkynyl.

In certain embodiments, X is a straight chain aliphatic group containing 2 carbons, wherein the aliphatic group is substituted with 2 $-OR^a$ groups; wherein $R^a$ is a $-(C_8-C_{12})$alkyl.

The Variables "Y" and "Z"

As described herein, Y is $-C(=O)-$, $-C(=S)-$, or is absent; and Z is O, S or NH.

Accordingly, in certain embodiments, Y is $-C(=O)-$. In certain embodiments, Y is $-C(=S)-$. In certain embodiments, Y is absent.

In certain embodiments, Z is O. In certain embodiments, Z is S. In certain embodiments, Z is NH.

In certain embodiments, a specific value for Y—Z is $-C(=O)NH-$, $-C(=O)O-$ or $-C(=S)O-$. Another specific value for Y—Z is —C(=O)NH— or —C(=O)O—. Another specific value for Y—Z is —C(=O)O—.

The Variable "$R_1$": the Polyether

As used herein, the term polyether includes poly(alkylene oxides) having between about 2 and about 150 repeating units. Typically, the poly(alkylene oxides) have between about 50 and about 120 repeating units (e.g. 113 repeating units). The alkylene oxide units contain from 2 to 10 carbon atoms and may be straight chained or branched. The alkylene oxide units may contain from 2 to 10 carbon atoms. Poly(ethylene glycol) (PEG) is one embodiment. Alkoxy-, amino-, carboxy-, and sulfo-terminated poly(alkylene oxides) are preferred, with alkoxy-terminated (e.g., methoxy-terminated) poly(alkylene oxides) being one embodiment. Accordingly, in certain embodiments, the polyether is a methoxy terminated poly(ethylene glycol).

In certain embodiments, $R_1$ is:

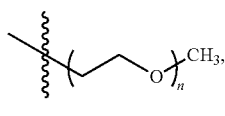

wherein n is about 2 to about 150. In certain embodiments, n is about 110 to about 120 (e.g., 110, 111, 112, 113, 114, 115, 116, 117, 118, 119 or 120). In certain embodiments, n is about 113.

In another embodiment of the invention a bioactive agent, such as a therapeutic agent can be attached to the $R_1$ group of a compound of formula I. The bioactive agent can be attached to the $R_1$ group through any suitable functional group. Suitable functional groups include but not limited to amides, esters, sulfonamides, sulfonates, anhydrides.

Certain Specific Embodiments

In certain embodiments, the compound of formula (I) is selected from:

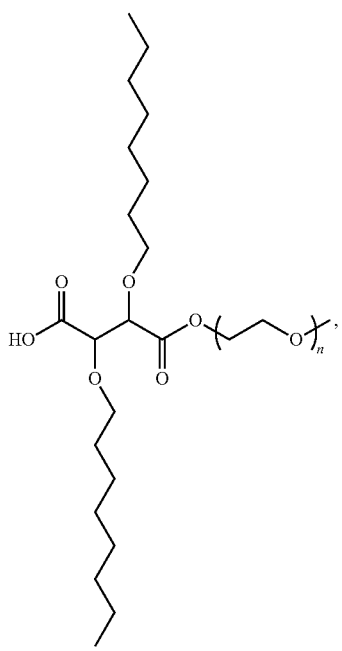

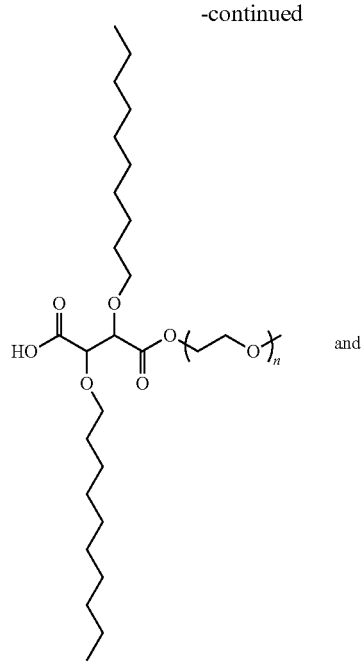

and

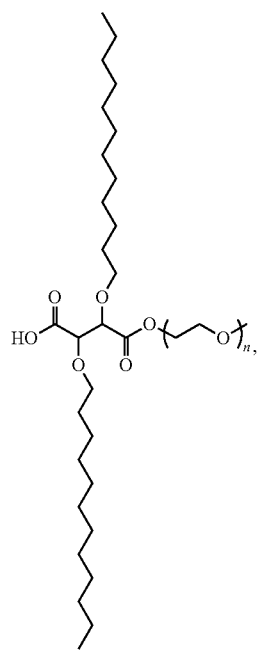

wherein n is about 2 to about 150. In certain embodiments, n is about 110 to about 120 (e.g., 110, 111, 112, 113, 114, 115, 116, 117, 118, 119 or 120). In certain embodiments, n is about 113.

In certain embodiments, the compound of formula (I) is selected from:

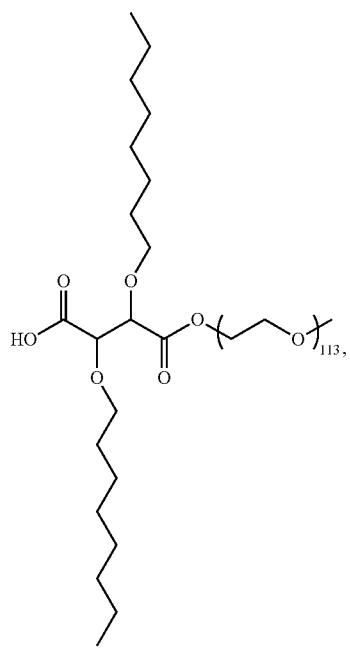

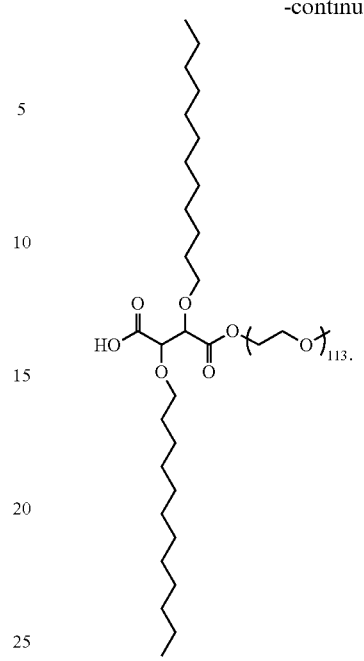

In certain embodiments, the compound of formula (I) is:

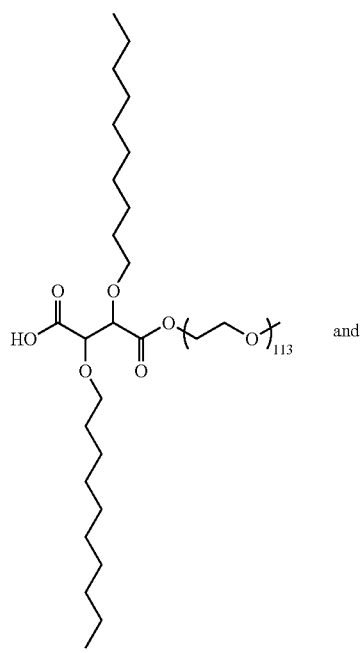 and

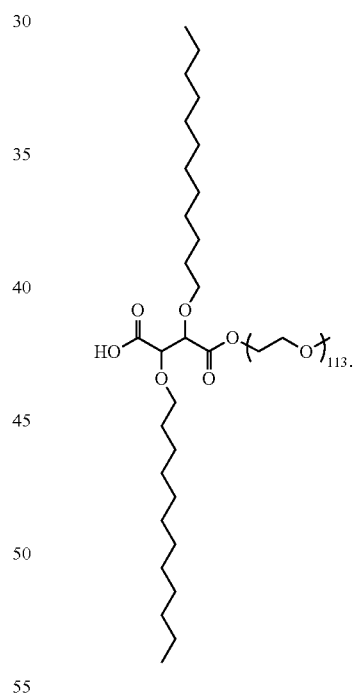

Aggregates and Encapsulates of the Invention

When a plurality of compounds of formula (I) are placed in a hydrophilic solvent (e.g., an aqueous solution comprising water or wherein the solvent is water), Applicant has discovered that the compounds of formula (I) will aggregate, with the polyether portion of the compounds extending into the hydrophilic solvent, and the hydrophobic chain portions of the compounds forming a hydrophobic core. Such aggregates can solubilize a hydrophobic molecule (e.g., a hydrophobic bioactive agent, such as a therapeutic agent) in the aqueous solvent, by encapsulating the hydrophobic molecule in the hydrophobic core of the aggregates. The hydrophobic molecule can typically be added to the solution of the compounds of formula (I) subsequent to aggregation, or the hydrophobic molecule can be added to the solution of the compounds of formula (I) prior to aggregation, allowing the aggregates to form around the molecule. Thus, the aggregates formed from the compounds of formula (I) can function similar to traditional micelles and can be used for essentially any application in which conventional micelles are employed (such as, e.g., drug solubilization, fragrance encapsulation, passive targeting for drug delivery, waste water treatment, enhanced capillary electrophoresis activation, and induction of protein crystallization). Thus, the compounds of formula (I) are useful as intermediates for preparing such aggregates.

In one embodiment, the aggregates of the invention have a diameter of from about 10 nm to about 1000 nm. The diameters can be measured using any suitable analytical technique, such as, for example, dynamic light scattering.

Accordingly, as used herein, the term "aggregate" means a plurality of compounds of formula (I) in a solvent that have organized into an ordered structure, for example, a structure having a hydrophobic core and a surrounding hydrophilic layer, or a structure having a hydrophilic core and a surrounding hydrophobic layer.

As used herein, the term "a plurality of compounds of formula (I)" means more than one compound of formula (I). In such a plurality, each compound of formula (I) can have the same structure, or the plurality can include compounds of formula (I) that have differing structures. In a specific embodiment, the term "a plurality of compounds of formula (I)" means more than one compound of formula (I), wherein each of the compounds of formula (I) has the same structure.

Certain embodiments of the invention provide a composition comprising a plurality of compounds of formula (I), as described herein, in a solvent, wherein the compounds of formula (I) form one or more aggregate structures.

In certain embodiments, the solvent comprises water.

In certain embodiments, the solvent is water.

Certain embodiments of the invention provide an aggregate structure comprising a plurality of compounds of formula (I) as described herein, and a solvent.

Certain embodiments of the invention provide a method for preparing an aggregate structure, comprising combining a plurality of compounds of formula (I), as described herein, in a solvent; and allowing them to form the aggregate structure.

Certain embodiments of the invention provide an aggregate formed by the method described in herein.

In one embodiment, the invention provides a composition comprising a plurality of compounds of formula (I) and one or more lipids.

The invention also provides an encapsulate comprising a molecule (e.g. a bioactive agent, such as a therapeutic agent) surrounded or partially surrounded by an aggregate of the invention.

As used herein, the term "encapsulate" means an aggregate, having a molecule (e.g., a bioactive agent, such as a therapeutic agent) surrounded or partially surrounded by a plurality of compounds of formula (I). In certain embodiments, the term "encapsulate" means an aggregate, having a molecule (e.g., a bioactive agent, such as a therapeutic agent) surrounded or partially surrounded by a plurality of compounds of formula (I) and one or more lipids.

As used herein, the term "stabilized encapsulate" means an aggregate, having a molecule (e.g., a bioactive agent, such as a therapeutic agent) surrounded or partially surrounded by a plurality of compounds of formula (I). In certain embodiments, the term "stabilized encapsulate" means an aggregate, having a molecule (e.g., a bioactive agent, such as a therapeutic agent) surrounded or partially surrounded by a plurality of compounds of formula (I) and one or more lipids.

The invention also provides a method for preparing an encapsulate of the invention comprising combining a) a plurality of compounds of formula (I), as described herein; b) a molecule (e.g. a bioactive agent, such as a therapeutic agent); and c) a solvent; and allowing the compounds of formula (I) to aggregate around the molecule, to provide the encapsulate.

Certain embodiments of the invention provide an encapsulate prepared by a method described herein.

The invention also provides a composition comprising a solvent, and an aggregate of a plurality of compounds of formula (I) surrounding a molecule (e.g., a bioactive agent, such as a therapeutic agent).

The invention also provides a pharmaceutical composition comprising an encapsulate of the invention (e.g., a therapeutic agent surrounded or partially surrounded by a plurality of compounds of formula (I)), or a pharmaceutically acceptable salt thereof, and a pharmaceutically acceptable carrier.

The invention also provides a method for delivering a therapeutic agent to an animal (e.g., a human) in need of treatment with the agent comprising administering an encapsulate of the invention, or a pharmaceutically acceptable salt thereof, comprising the agent to the animal.

As used herein, the term "molecule" includes any compound that can be incorporated into an aggregate as described herein. Typically, "molecules" have solubility properties that are undesirable and that can be modified by incorporation into an aggregate of the invention. For example, the term "molecule" includes bioactive agents, such as therapeutic agents (e.g., an agent that may be used to treat atherosclerosis or inflammation). The term "molecule" also includes, insecticides, pesticides, herbicides, antiseptics, food additives, fragrances, dyes, diagnostic aids, and the like. Other specific examples of molecules include, but are not limited to:

abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allyl sulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene;

baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bomyl, bromoisovalerate, bomyl chloride, bomyl isovalerate, bornyl salicylate, brodifacoum, bromethalin, broxyquinoline, bufexamac, butamirate, butethal, buthiobate, butlated hydroxyanisole, butylated hydroxytoluene;

calcium iodostearate, calcium saccharate, calcium stearate, capobenic acid, captan, carbamazepine, carbocloral, carbophenothin, carboquone, carotene, carvacrol, cephaeline, cephalin, chaulmoogfic acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofazimine, clofibrate, cloflucarban, cionitrate, clopidol, clorindione, cloxazolam, coroxon, corticosterone, coumachlor, coumaphos, coumithoate cresyl acetate, crimidine, crifomate, cuprobam, cyamemazine, cyclandelate, cyclarbamate cymarin, cypennethril;

dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicmarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicofinamide, dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscomacetate, ethylhydrocupreine, ethyl menthane carboxamide, eugenol, euprocin, exalamide;

febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, flurothyl, flutazolam, fumagillin, 5-furfuryl-5-isopropylbarbitufic acid, fusafungine, glafenine, glucagon, glutethimide, glybuthiazole, griseofulvin, guaiacol carbonate, guaiacol phosphate, halcinonide, hematoprphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione;

josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenytoin, meprylcaine, mestanolone, mestranol, mesulfen, metergoline, methallatal, methandriol, methaqualone, 3-methylcholanthrene, methylphenidate, 17-methyltestosterone, metipranolol, minaprine, myoral, nafialofos, nafiopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone;

octavefine, oleandrin, oleic acid, oxazepam, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarbamide, pheniramine, 2-phenyl-6-chlorophenol, phentlmethylbarbituric acid, phenytoin, phosalone, phthalylsulfathiazole, phylloquinone, picadex, pifarnine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate;

quercetin, quinbolone, quizalofo-ethyl, rafoxanide, rescinnamine, rociverine, ronnel salen, scarlet red, siccmn, simazine, simetfide, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thiocftc acid, thioquinox, thioridazine, thiram, thymyl N-isoamylcarbamate, tioxidazole, tioxolone, tocopherol, tolciclate, tolnafiate, triclosan, triflusal, triparanol;

ursolic acid, valinomycin, verapamil, vinblastine, vitamin A, vitamin D, vitamin E, xenbucin, xylazine, zaltoprofen, and zearalenone.

The aggregates of the invention are particularly useful for solubilizing hydrophobic molecules, particularly therapeutic agents that are hydrophobic in nature. Thus, according to one embodiment of the present invention, a therapeutic agent is encapsulated by combining the agent and a plurality of compounds of formula (I) in a solvent, such as water. The present invention contemplates the use of encapsulated hydrophobic molecules at concentrations ranging from $10^{-3}$ to $10^{-6}$ M. At the same time, another advantage of the present invention is the thermodynamic stability of the polymers, which permit the formation of low concentration stable aqueous solutions of the polymer encapsulates, far below the CMC's of conventional surfactants. CMC values range from $10^{-4}$ to $10^{-7}$ M but may be as low as $10^{-10}$ which may be below detection limits. CMC is the critical micellar concentration, the concentration at which a majority of the polymers are comprised within micellar aggregates vs. individual polymer chains.

Methods of Use

As described herein, compounds of formula I can inhibit the uptake of modified forms of LDL mediated by scavenger receptors (e.g., scavenger receptor A (SR-A) or CD36) and counteract cholesterol accumulation and foam cell formation, characteristics of the onset of atherogenesis. In certain embodiments, a compound of formula I competitively inhibits scavenger receptor-mediated LDL uptake. In certain embodiments, a compound of formula I competitively inhibits scavenger receptor-mediated LDL uptake in macrophages.

Accordingly, certain embodiments of the invention provide a method for inhibiting LDL (e.g., oxLDL) uptake by a cell, comprising contacting the cell in vitro or in vivo with an effective amount of a compound of formula (I) as described herein, or a pharmaceutically acceptable salt thereof. In certain embodiments, the cell is a mammalian cell. In certain embodiments, the cell is a macrophage or a smooth muscle cell.

In certain embodiments, the cell expresses a scavenger receptor (e.g., SR-A or CD36).

In certain embodiments, a compound of formula (I) interacts with the scavenger receptor. In certain embodiments, a compound of formula (I) binds to the scavenger receptor.

Certain embodiments of the invention provide a method of preventing foam cell formation in a mammal, comprising administering to the mammal an effective amount of a compound of formula (I), or a pharmaceutically acceptable salt thereof, or an aggregate or an encapsulate as described herein.

Certain embodiments of the invention provide a method for inhibiting atherosclerosis or atherosclerotic development in a mammal comprising administering to the mammal an effective amount of a compound of formula (I), or a pharmaceutically acceptable salt thereof, or an aggregate or an encapsulate as described herein.

Certain embodiments of the invention provide a compound of formula I or a pharmaceutically acceptable salt thereof, or an aggregate, or an encapsulate as described herein for the prophylactic or therapeutic treatment of atherosclerosis.

Certain embodiments of the invention provide a compound of formula I, or a pharmaceutically acceptable salt thereof, or an aggregate or an encapsulate as described herein for use in medical treatment.

Certain embodiments of the invention provide the use of a compound of formula I as described herein or a pharmaceutically acceptable salt thereof, or an aggregate or an encapsulate as described herein for the preparation of a medicament for inhibiting atherosclerosis or atherosclerotic development in a mammal.

Another embodiment provides a compound of the following formula:

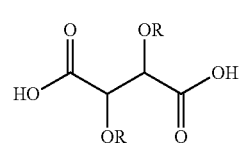

wherein each R is independently selected from the group consisting of $(C_7-C_{12})$alkyl and $(C_7-C_{12})$alkanoyl.

In one embodiment each R is independently selected from the group consisting of $(C_7-C_{12})$alkyl.

In one embodiment each R is independently selected from the group consisting of $(C_8)$alkyl, $(C_{10})$alkyl, $(C_{12})$alkyl, $(C_8)$alkanoyl, $(C_{10})$alkanoyl and $(C_{12})$alkanoyl.

In one embodiment each R is independently selected from the group consisting of $(C_{12})$alkyl and $(C_{12})$alkanoyl.

In one embodiment each R is independently selected from the group consisting of $(C_8)$alkyl, $(C_{10})$alkyl and $(C_{12})$alkyl.

In one embodiment each R is independently selected from the group consisting of $(C_{12})$alkyl.

In one embodiment each R is $-(CH_2)_{11}CH_3$.

In one embodiment each R is independently selected from the group consisting of $(C_6)$alkyl, $(C_8)$alkyl, $(C_{10})$alkyl, $(C_6)$alkanoyl, $(C_8)$alkanoyl and $(C_{10})$alkanoyl.

Pharmaceutical Compositions and Administration

Certain embodiments of the invention provide a pharmaceutical composition comprising a compound of formula (I), or a pharmaceutically acceptable salt thereof, or an aggregate or an encapsulate as described herein and a pharmaceutically acceptable carrier.

Administration of a compound of formula I as a pharmaceutically acceptable acid or base salt may be appropriate. For example, alkali metal (e.g. sodium, potassium or lithium) or alkaline earth metal (e.g. calcium) salts of carboxylic acids, sulfonic acids, sulfonamides or other anionic groups can be made. Examples of pharmaceutically acceptable salts also include organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Thus, the compounds of formula (I), or a pharmaceutically acceptable salt thereof, aggregates and encapsulates of the invention can be formulated as pharmaceutical compositions and administered to a mammalian host, such as a human male or female patient in a variety of forms adapted to the chosen route of administration, e.g., orally or parenterally, by intravenous, intramuscular, topical or subcutaneous routes. In certain embodiments, the compounds of formula (I), aggregates or encapsulates of the invention will be administered via solution, e.g., nasally, in eye drops, or via injection, and not orally.

The compounds of formula (I), aggregates and encapsulates of the invention may be administered intravenously or intraperitoneally by infusion or injection. Solutions of the compounds of formula (I), aggregates and encapsulates of the invention can be prepared, for example, in water. Under ordinary conditions of storage and use, these preparations may contain a preservative to prevent the growth of microorganisms.

The pharmaceutical dosage forms suitable for injection or infusion should be sterile, fluid and stable under the conditions of manufacture and storage. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the compounds of formula (I), aggregates or encapsulates of the invention in the required amount in the appropriate solvent with various of the other ingredients enumerated above, as required, followed by sterilization.

The dose and method of administration will vary from animal to animal and be dependent upon such factors as the type of animal being treated, its sex, weight, diet, concurrent medication, overall clinical condition, the particular therapeutic agent employed, the specific use for which the agent is employed, and other factors which those skilled in the relevant field will recognize.

Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the patient. The determination of effective dosage levels, that is, the dosage levels necessary to achieve the desired result, will be within the ambit of one skilled in the art. Typically, applications of agent are commenced at lower dosage levels, with dosage levels being increased until the desired effect is achieved. Advantageously, the dosage forms of this invention may administered several times daily, and other dosage regimens may also be useful.

General Terminology

Halo refers to fluoro, chloro, bromo, or iodo.

Alkyl, alkene, alkyne, alkoxy, etc. denote both straight and branched groups; but reference to an individual radical such as propyl embraces only the straight chain radical, a branched chain isomer such as isopropyl being specifically referred to.

The term "alkyl," as used herein, denotes a linear or branched-chain hydrocarbon group.

The term "alkenyl," as used herein, denotes a linear or branched-chain hydrocarbon group with one or more (e.g., 1, 2, 3 or 4) carbon-carbon double bonds.

The term "alkynyl," as used herein, denotes a linear or branched-chain hydrocarbon group with one or more (e.g., 1, 2, 3 or 4) carbon-carbon triple bonds.

Alkoxy refers to the group —O-alkyl (e.g. a group wherein a alkyl radical is connected to a molecule through an oxygen atom).

Carboxy refers to $-CO_2H$.

As used herein, the phrase "low-density lipoprotein (LDL)" includes "unoxidized LDL," "weakly oxidized LDL" and "oxidized LDL." LDLs bind to proteoglycans (PGs), the major low density lipoprotein (LDL)-retentive matrix molecules within the vascular intima are proteoglycans. LDL binding to PGs modifies the LDL surface, rendering the LDL susceptible to oxidation induced by $Cu^{2+}$ and macrophages. The oxidative modification of LDL lowers its localized positive charge relative to native LDL, thus reducing the affinity of LDL for anionically charged PGs. The increase in the net negative charge on oxidized LDL also leads to the reduced recognition of oxidized LDL by the classical LDL receptor, and increased recognition by the scavenger receptors on macrophages in the intima. Thus, "unoxidized low-density lipoprotein" refers to a native LDL, e.g., an LDL that has the characteristics of an LDL that is recognized by a native LDL receptor. In contrast, an "oxidized LDL (ox-LDL)" is a modified LDL recognized by scavenger receptors. By the phrase "weakly oxidized low-density lipoprotein (LDL)" is meant a mildly or partially oxidized LDL. Both unoxidized and weakly oxidized LDL have relatively high localized positive charges, e.g., due to unmodified Lys and Arg residues on apolipoprotein B-100 (ApoB-100) (LDL have a single Apo B-100 molecule on their surface) as compared to oxidized LDL. See, for example, Chnari et al., Biomaterials, 26: 3749-3758 (2005) and Chnari et al., Biomacromolecules. 2006 February; 7(2): 597-603.

By "inhibition of atherosclerotic development" is meant the suppression of the development, progression and/or severity of atherosclerosis, a slowly progressive disease characterized by the accumulation of cholesterol within the arterial wall, e.g. by inhibiting, preventing or causing the regression of an atherosclerotic plaque.

The invention also provides the process for preparing the compound T(12-O)P5 illustrated below.

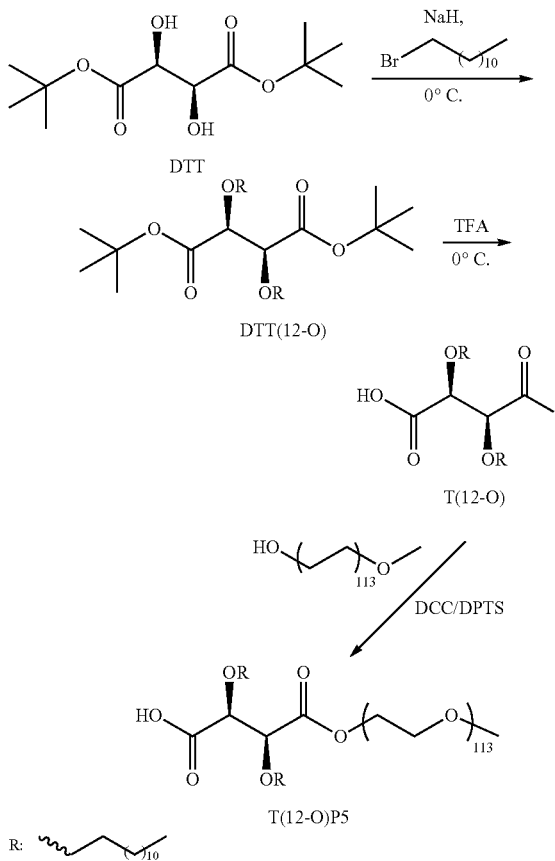

Certain embodiments of the invention will now be illustrated by the following non-limiting Examples.

EXAMPLE 1

Sugar-based Amphiphilic Macromolecules with Ether Linkages Exhibit Enhanced Repression of Oxidized Low Density Lipoprotein Uptake Cardiovascular disease initiates with the atherogenic cascade of oxidized low density lipoprotein (oxLDL) uptake and the resulting foam cell formation leads to lipid-rich lesions within arterial walls. As described herein, sugar-based amphiphilic macromolecules (AMs) were designed to inhibit these processes by competitively blocking scavenger receptors (SR), thus, potentially arresting the development of atherosclerosis. The amphiphilicity imparted by the hydrophobic arms and the resulting 3-D conformations of the sugar component were previously determined to have significant effects on anti-atherogenic potency. As described below, the impact of replacing the ester linkages with ether linkages in the hydrophobic domain was investigated. A series of sugar-base AMs with varying hydrophobic chain lengths and conjugation chemistries were synthesized, chemically and physically characterized, and then evaluated for their impact on biological activity. Notably, AMs with ether linkages exhibited significantly higher (90%) levels of inhibition of oxLDL uptake, indicating a dominant effect of chain flexibility on pharmacological activity. This study further suggests that alkyl chain length (i.e, relative hydrophobicity) and stereochemistry (i.e., orientation) play an important role in modulating oxLDL uptake, and guide the design of innovative cardiovascular therapies.

Introduction

Cardiovascular diseases are the leading cause of mortality in developed countries (Li, A. C.; Glass, C. K., Nat. Med. 2002, 8 (11), 1235-1242; Lloyd-Jones, D et al., Circulation 2010, 121 (7), e46-e215). Atherosclerosis, defined as the buildup of lipid rich plaques within the vascular intima, is the foremost pathology underlying these conditions. This process initiates with accumulation of oxidized low density lipoproteins (oxLDL) within the vessel walls, triggering monocyte recruitment, diapedesis and differentiation to macrophages, which subsequently uptake oxLDL via scavenger receptors. This unregulated uptake of oxLDL leads to formation of foam cells and secretion of inflammatory mediators (Yoshimoto et al., Advances in experimental medicine and biology 2002, 507, 403-7). The atherogenic accumulation of lipid laden macrophages results in plaques that can exhibit the clinical endpoints of myocardial infarction, stroke or peripheral arterial disease.

Traditional therapies to reduce vascular lipid burden focus on lowering the hepatic synthesis of cholesterol, however, these therapies fail to target lesion development. An alternative approach to address this problem is through direct inhibition of oxLDL uptake via macrophage SRs and prevention of the ensuing inflammatory steps. Sugar-based amphiphilic macromolecules (AMs) with hydrophobic chains and a hydrophilic tail (comprised of poly(ethylene glycol); PEG) were developed as biocompatible micelle-forming amphiphiles (FIG. 1). AMs have shown promising results as anti-atherogenic agents by selectively inhibiting oxLDL uptake (FIG. 1) (Chnari et al., Biomacromolecules 2006, 7 (2), 597-603; Chnari et al., Biomaterials 2005, 26 (17), 3749-58; Iverson, et al., Biomaterials 2011, 32 (32), 8319-27; Iverson, et al., Acta biomaterialia 2010, 6 (8), 3081-91). By varying specific structural motifs of the AMs, a number of important features were identified as influencing the anti-atherogenic activity. These modifications included variations in the free carboxylic acid (location and frequency), nature of the sugar backbone (stereochemistry and branching), hydrophobic chains (degree of branching and chain length), and PEG (molecular weight (Mw) and branching) (Iverson, et al., Acta Biomater 2010, 6 (8), 3081-3091). Detailed studies have shown that seemingly minor changes in the chemical structure, stereochemistry, degree of branching, and/or hydrophobicity of the aliphatic chains had a considerable effect on bioactivity (Iverson, et al., Acta biomaterialia 2010, 6 (8), 3081-91; Poree, et al., Biomacromolecules 2013, 14 (8), 2463-9). Further, molecular modeling studies suggested that AMs competitively inhibit oxLDL uptake by SRs via electrostatic and hydrophobic interactions (Plourde, et al., Biomacromolecules 2009, 10 (6), 1381-91). The 3D conformation of AMs in solution, specifically the extension of the hydrophobic arms, was found to be important for inhibition efficacy (Lewis, et al., Biomaterials 2013, 34 (32), 7950-7959).

While the chain length and hydrophobic domain branching has been established for activity, the potential role of the linkage chemistry with respect to the sugar backbones has not been systematically studied. The ester linkages between the sugar backbone and the hydrophobic chains are characterized by the partial double bond character of the ester bond that restricts movement. This conformational rigidity may govern the nature of the three-dimensional conformation, which may ultimately affect the binding capacity of AMs to the SRs. Additionally, as the ester linkages are vulnerable to hydrolysis by esterases (Bahar Demirdirek, MS Dissertation in Chemistry (January 2009), Rutgers University, "Synthesis and Evaluation of Amphiphilic Scorpion-like and Star Macromolecules for Biomedical Applications"), whether more stable compounds with ether linkages can overcome this limitation and exhibit enhanced bioactivity was examined as described below.

Susceptibility to esterase hydrolysis is an important consideration in drug design (Casey Laizure et al., *Pharmacotherapy: The Journal of Human Pharmacology and Drug Therapy* 2013, 33 (2), 210-222). Esterases are principally expressed in liver and to a lesser extent in the plasma, kidney and small intestine. Responsible for 10% of all drug metabolism, esterase activity can significantly decrease drug efficacy (Fukami, T.; Yokoi, T., *Drug Metab. Pharmacokinet.* 2012, 27 (5), 466-77). Different esterases preferentially hydrolyze separate classes of ester bond substrates and many prodrugs rely on esterase activity for drug activation. Additionally, interpatient differences in esterase expression can result in highly variable drug efficacy (Hosokawa, et al., *Drug Metab. Dispos.* 1995, 23 (10), 1022-7). Of specific concern to develop AMs for inhibition of scavenger receptor uptake of oxLDL, monocytes and macrophages have significant expression of the esterase Carboxylesterase1 (Needham, et al., *J. Pharmacol. Exp. Ther.* 2011, 339 (1), 132-142). As these are target cells for atherogenesis, it is critical to design molecules that resist rapid degradation; ether bonds were investigated as described herein.

Figure 2:
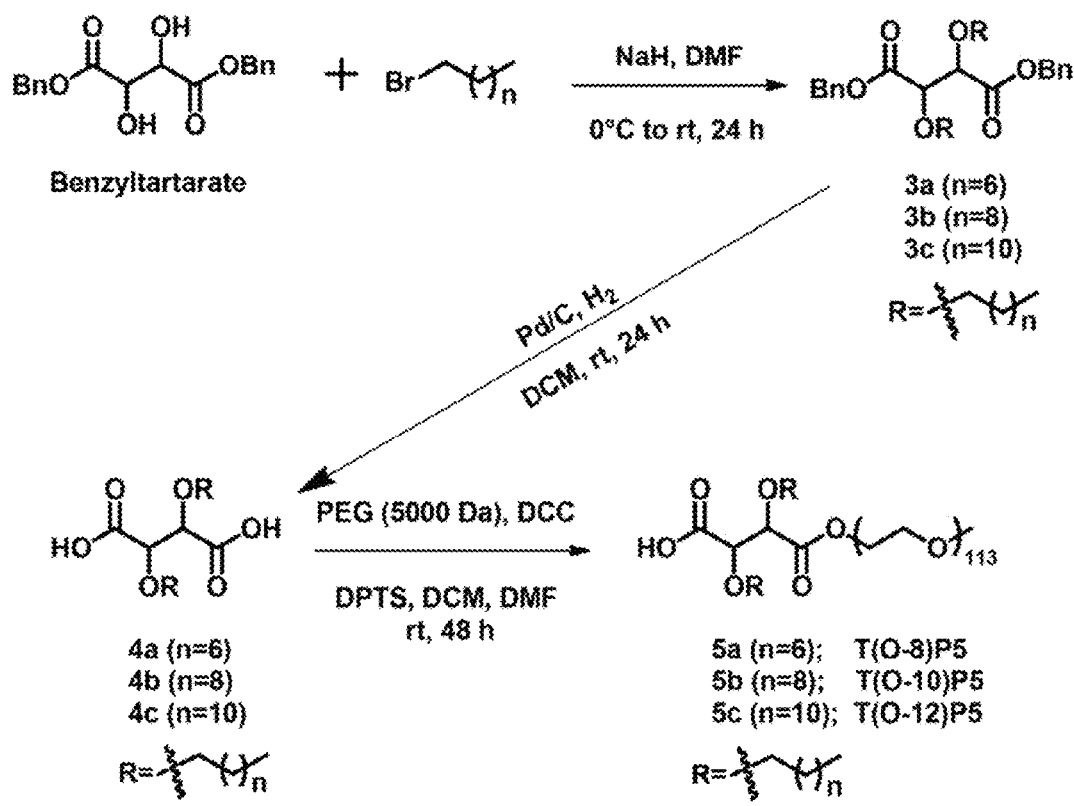
FIG. 2. Scheme for synthesis of the ether analogs.
Figure 3:
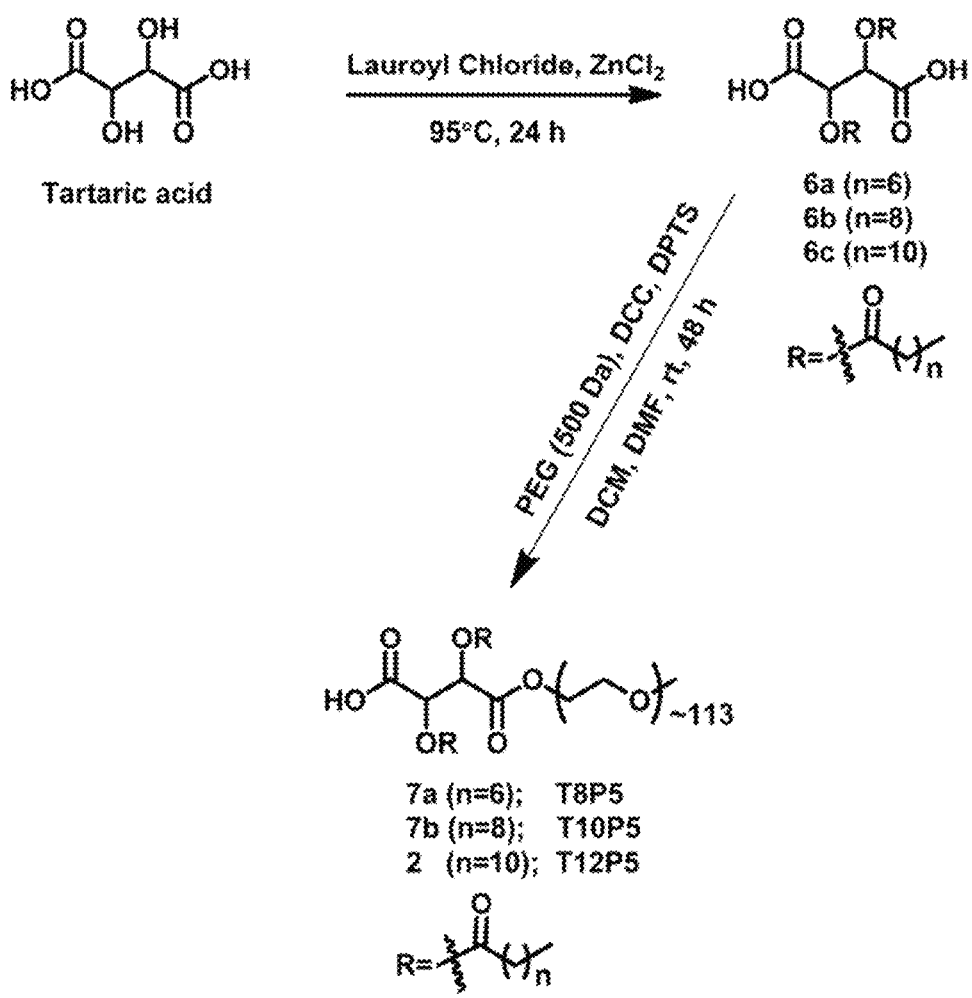
FIG. 3. Scheme for synthesis of the ester analogs.

Further, it was hypothesized that replacing ester linkages by ether linkages would increase rotation around the ester C—O single bond, which is relatively rigid due to the partial double bond resonance. The increased conformational flexibility afforded by the ether linkage could allow tighter alignment of the hydrophobic arms, potentiating a better fit within the SR binding pocket, and offering enhanced binding affinity. In this study, novel ether-containing analogs were designed based on a tartaric acid backbone with two hydrophobic chains (3 a-c). In previous work, the most potent AM was based on a mucic acid backbone with ester-linked alkyl chains (FIG. 1, compound (1)). Thus, for direct comparison and to clearly delineate the ester/ether effect, we synthesized tartaric acid-based ester analogues (FIG. 1, compound (2); FIG. 3, compounds 7a and 7b) as well as the ether-based tartaric acid-analogs (FIG. 2, compounds 5a-c).

Herein, the synthetic strategy for preparing analogous ether- and ester-linked AMs, a comparison of the associated physicochemical properties, and finally their biological evaluation are presented. Specifically, the ability to inhibit oxLDL uptake and foam cell formation in human, peripheral blood mononuclear cells (PBMCs) under serum-free conditions was examined. Additionally, the most active compounds were compared to the most potent ester-based AMs reported to date. Replacing the ester linkages with ether bonds-holding chain length constant—decouples their influence on the physicochemical properties and biological activity.

2. Materials and Methods
2.1. Materials

Reagents (tartaric acid, zinc chloride, lauroyl chloride, octyl chloride, decanoyl chloride, sodium hydride (NaH), bromooctane, bromodecane, bromododecane, dimethyl amino pyridine (DMAP), p-toluene sulphonic acid, N,N'-dicyclohexylcarbodiimide (DCC), and HPLC grade solvents were purchased from Sigma-Aldrich and used directly unless otherwise mentioned. Dibenzyl tartrate was purchased from TCI. Dimethyl amino pyridine p-toluene sulphonate (DPTS) was prepared as previously published. Before use monomethoxy-poly(ethylene glycol) (mPEG, $M_n$=5000 Da) was azeotropically distilled with toluene to remove water (3×50 mL) and dried under high vacuum for 4 hours. 18 MΩ·cm resistivity deionized (DI) water was obtained using PicoPure 2 UV Plus (Hydro Service and Supplies. Durham, N.C.). The following items were purchased from the indicated vendors: 1.077 g/cm3 Ficoll-Paque Premium from GE healthcare (Pittsburgh, Pa.), RPMI 1640 from ATCC (Manassas, Va.), macrophage colony stimulating factor (M-CSF) from PeproTech (Rocky Hill, N.J.), FBS from Life Technologies (Grand Island, N.Y.), unlabeled oxLDL from Biomedical Technologies Inc. (Stoughton, Mass.), 3,3'-dioctadecyloxacarbocyanine (DiO) labeled oxLDL from Kalen Biomedical (Montgomery Village, Md.), and human buffy coats from the Blood Center of New Jersey (East Orange, N.J.).

2.2. Instrumentation

Chemical structures were confirmed by $^1$H NMR spectra recorded on either a Varian VNMRS 400 MHz or 500 MHz spectrometer. Samples were dissolved in $CDCl_3$ containing tetramethylsilane (TMS) as an internal reference. IR spectra were recorded in $CHCl_3$ on a Thermo Nicolet/Avatar 360 spectrophotometer using OMNIC software by solvent-casting onto a NaCl plate. Each spectrum was an average of 32 scans. Mass spectrometry was performed using ThermoQuest Finnigan LCQ-DUO system equipped with syringe pump, atmospheric pressure ionization (API) source, mass spectrometer (MS) detector, and X calibur data system. Samples were prepared in spectrophotometric grade MeOH at a concentration of 10 μg/ml. Molecular weight (MW) was determined by gel permeation chromatography using a Waters LC system (Milford, Mass.) with a 2414 refractive index detector, a 1515 isocratic HPLC pump, and 717 plus autosampler equipped with a PL-Gel column. HPLC grade tetrahydrofuran (THF) was used as eluent for analysis and for sample preparation. The sample (10 mg/mL) was dissolved into THF and filtered using a 0.45 μm PTFE syringe filter (Whatman, Clifton, N.J.) before injection into the column at a flow rate of 0.5 mL/min. The average MW of the sample was calibrated against narrow molecular weight PEG standards (Sigma-Aldrich) on a Waters Stryagel® HR 3 THF column (7.8×300 mm). Melting temperature was determined using a TA instrument Q200 by heating samples (4-8 mg) under dry nitrogen gas from −30° C. to 200° C. Data were collected at heating and cooling rates of 10° C./min with a three-cycle minimum then analyzed using TA Instruments Universal Analysis 2000 software version 4.5 A. Hydrodynamic diameter and zeta potential were determined using a Zetasizer nanoseries ZS90 (Malvern Instruments, UK). Samples were prepared using HPLC grade water at a concentration of (10 mg/mL) and filtered through 0.45 μm PTFE syringe filters before measurement. Each sample was run three times separately at room temperature with 20 measurements per run. Critical micelle concentration (CMC) measurements were carried out by fluorescence studies on a Spex fluoro Max spectrofluorometer at 25° C. A stock solution of $5\times10^{-7}$M pyrene in water was prepared and used as the probe molecule. Samples were dissolved in water, diluted to specific concentrations, and then added to the stock pyrene solution. Excitation was performed from 300 to 360 nm, with 390 nm as the emission wavelength. Upon micelle formation, the pyrene maximum absorption shifted from 332 to 334.5 nm. The ratio of absorption of pyrene with polymer (334.5 nm) to pyrene only (332 nm) was plotted as the logarithm of polymer concentrations and the inflection point was taken as the CMC value.

2.3. Synthesis 2.3.1: General Procedure for Synthesis of Alkylated Benzyl Tartrates (Compounds 3 a-c)

Into an oven dried (cooled under Ar(g)) 100 mL three necked round bottom flask (RBF), 10 mL anhydrous DMF were transferred then cooled to −10° C. using ice bath. NaH (636 mg, 8 mmol) was cautiously added followed by dropwise addition of benzyltartrate solution (1.36 gm, 4 mmol in 10 mL of DMF) over 15 minutes. The reaction was stirred for 30 minutes then the alkylating reagent (8.4 mmol) was added. The reaction was allowed to warm to room temperature and stirred for 16 hours. The reaction was quenched with saturated $NH_4Cl$ solution and extracted three times with ethyl acetate. Combined organic layers were dried over anhydrous $Na_2SO_4$ crystals. After filtration and solvent evaporation to dryness, the product was isolated by flash column chromatography using 95:5 hexane:ethylacetate as eluent.

Compound 3a

Colorless oil (244 mg, 11%). IR (cm$^{-1}$, thin film from CHCl$_3$): 2926, 2855, 1761, 1735. $^1$H-NMR (CDCl$_3$): δ=7.34 (m, 10), 5.21 (d, 2), 5.15 (d, 2), 4.35 (s, 2), 3.70 (m, 2), 3.20 (m, 2), 1.47 (m, 4), 1.24 (m, 20), 0.86 (t, 6). $^{13}$C-NMR (CDCl$_3$): 169.62, 135.65, 128.61, 80.24, 72.77, 67.02, 32.06, 29.57, 26.10, 22.87, 14.32. [M+Na]$^+_{theo}$=577.7, GC-MS: [M+Na]$^+_{calc}$=577.8.

Compound 3b

Colorless oil (269 mg, 11%). IR (cm$^{-1}$, thin film from CHCl$_3$): 2924, 2854, 1762, 1734. $^1$H-NMR (CDCl$_3$): δ=7.33 (m, 10), 5.21 (d, 2), 5.15 (d, 2), 4.35 (s, 2), 3.70 (m, 2), 3.20 (m, 2), 1.47 (m, 4), 1.26 (m, 28), 0.86 (t, 6). $^{13}$C-NMR (CDCl$_3$): 169.62, 135.66, 128.65, 80.24, 72.77, 67.02, 32.15, 29.68, 26.08, 22.93, 14.34. [M+Na]$^+_{theo}$=633.8, GC-MS: [M+Na]$^+_{calc}$=633.3.

Compound 3c

Colorless oil (293 mg, 10%). IR (cm$^{-1}$, thin film from CHCl$_3$): 2924, 2853, 1762, 1735. $^1$H-NMR (CDCl$_3$): δ=7.33 (m, 10), 5.22 (d, 2), 5.14 (d, 2), 4.35 (s, 2), 3.71 (m, 2), 3.20 (m, 2), 1.47 (m, 4), 1.24 (m, 20), 0.87 (t, 6). $^{13}$C-NMR (CDCl$_3$): 169.62, 135.65, 128.76, 80.24, 72.77, 67.02, 32.15, 29.75, 26.10, 22.91, 14.34. [M+Na]$^+_{theo}$=689.4, GC-MS: [M+Na]$^+_{calc}$=689.7.

2.3.2: General Procedure for Hydrogenolysis (Synthesis of Compounds 4 a-c)

Alkylated product (0.5 mmol) was transferred into 50 mL RBF and dissolved in 10 mL anhydrous DCM. 10% w/w Pd/C (10 mole %) was added, and the reaction was stirred under H$_2$ gas for 24 hours. After all starting material was consumed the reaction was filtered over a pad of celite and washed several times with DCM. $^1$H-NMR spectrum of the residue obtained after removal of solvent by rotary evaporation showed clean product that was taken to the next step without further purification.

Compound 4a

Colorless oil (180 mg, 96%). IR (cm$^{-1}$, thin film from CHCl$_3$): 2923, 2854, 1728. $^1$H-NMR (CDCl$_3$): δ=4.37 (s, 2), 3.70 (m, 2), 3.51 (m, 2), 1.59 (m, 4), 1.26 (m, 20), 0.87 (t, 6). $^{13}$C-NMR (CDCl$_3$): 171.16, 79.64, 73.86, 31.99, 29.57, 29.45, 29.37, 25.95, 22.84, 14.29. [M+Na]$^+_{theo}$=397.5, GC-MS: [M+Na]$^+_{calc}$=397.8.

Compound 4b

Colorless oil (204 mg, 95%). IR (cm$^{-1}$, thin film from CHCl$_3$): 3444, 2922, 2852, 1645. $^1$H-NMR (CDCl$_3$): δ=4.38 (s, 2), 3.70 (m, 2), 3.51 (m, 2), 1.60 (m, 4), 1.16 (bs, 28), 0.88 (t, 6). $^{13}$C-NMR (CDCl$_3$): 170.98, 79.40, 73.68, 31.92, 29.71, 29.54, 29.37, 25.74, 22.68, 14.12. [M+Na]$^+_{theo}$=453.6, GC-MS: [M+Na]$^+_{calc}$=453.8.

Compound 4c

White solid (231 mg, 95%). IR (cm$^{-1}$, thin film from CHCl$_3$): 2919, 2850, 1746. $^1$H-NMR (CDCl$_3$): δ=4.38 (s, 2), 3.69 (m, 2), 3.59 (m, 2), 1.47 (m, 4), 1.25 (m, 20), 0.88 (t, 6). $^{13}$C-NMR (CDCl$_3$): 169.60, 79.33, 73.88, 31.92, 29.62, 29.48, 29.35, 25.73, 22.69, 14.12. [M+Na]$^+_{theo}$=509.7, GC-MS: [M+Na]$^+_{calc}$=509.9.

2.3.3: General Procedure for Coupling to PEG: (Synthesis of Compounds 5 a-c)

Using an established literature procedure (Tian, et al., Macromolecules 2004, 37 (2), 538-543), hydrogenolysis product (0.18 mmol), PEG (0.28 g, 0.06 mmol), DCC (1M in DCM) (0.192 mmol), and DPTS (0.02 g, 0.007 mmol) were used to yield the ether analogues. Briefly, PEG (5000) (0.28 g) was dehydrated by azeotropic distillation from toluene (25 mL) under vacuum. After cooling, PEG was dissolved in 2 mL anhydrous DCM. Hydrogenolysis product (0.18 mmol) and DPTS (0.02 g) were weighed into a 5 ml RBF and placed under argon. 2 mL Anhydrous DCM and 0.5 mL anhydrous DMF were then added to the round bottom flask to dissolve the reagents and the solution was then added at room temperature to PEG solution. After 10 min stirring under argon 0.192 mL DCC was added dropwise to the reaction flask over 15 minutes via syringe. The reaction mixture was stirred at room temperature under argon for 48 hours, cooled and the resulting white solid precipitate (DCC side product—dicyclohexylurea) was removed by vacuum filtration. The filtrate was washed with 0.1 N HCl, then twice with brine. The organic layer was dried over anhydrous Na$_2$SO$_4$, and evaporated to dryness. The crude product was purified by precipitation into diethyl ether (10 mL). The product was obtained as a white solid Compound 5a: T(O-8)P5

White powder (0.20 g, 65%). $^1$H NMR (CDCl$_3$): δ=4.32 (s, 2), 3.65 (m, ~400H), 1.68 (m, 8), 1.27(m, 20), 0.88 (t, 6); M$_w$=5.2 kDa; PDI=1.16.

Compound 5b: T(O-10)P5

White powder (0.22 g, 68%). $^1$H NMR (CDCl$_3$): δ=4.32 (s, 2), 3.65 (m, ~400H), 1.70 (m, 8), 1.25 (m, 28), 0.88 (t, 6); M$_w$=5.5 kDa; PDI=1.06.

Compound 5c: T(O-12)P5

White powder (0.22 g, 67%). $^1$H NMR (CDCl$_3$): δ=4.31 (s, 2), 3.65 (m, ~400H), 1.78 (m, 8), 1.25 (m, 36), 0.88 (t, 6); M$_w$=5.2 kDa; PDI=1.03.

2.3.4: General Procedure for Esterification: (Synthesis of Compounds 6 a-c)

Using a well-established literature procedure (Tian, et al., Macromolecules 2004, 37 (2), 538-543), briefly acid chloride (42 mL, 0.2 mol was added to tartaric acid (4.0 g, 27 mmol) and zinc chloride (1.1 g, 8.0 mmol) in 250 mL RBF. The reaction mixture was refluxed at 95° C. for 24 h. After cooling to room temperature, diethyl ether (20 mL) was added to the reaction mixture, and the solution was poured into ice water (150 mL) with stirring. Additional diethyl ether (80 mL) was added to the mixture and stirring continued for another 30 min. The ether portion was separated, washed three times with brine then dried over anhydrous sodium sulfate, and evaporated to dryness. The crude product was purified by precipitation into cold hexane (200 mL) then filtered and dried under vacuum.

Compound 6a:

Off-white powder (8.7 g, 56%). IR (cm$^{-1}$, thin film from CHCl$_3$): 3475, 2929, 1755, 1149. $^1$H-NMR (CDCl$_3$): δ=5.75 (s, 2), 2.43 (m, 4), 1.63 (m, 4), 1.30 (m, 16), 0.88 (t, 6). $^{13}$C-NMR (CDCl$_3$): 172.81, 70.23, 33.79, 31.82, 29.07, 29.03, 24.83, 22.78, 14.24. [M+Na]$^+_{theo}$=425.2, GC-MS: [M+Na]$^+_{calc}$=425.8.

Compound 6b:

Off-white powder (8.7 g, 56%). IR (cm$^{-1}$, thin film from CHCl$_3$): 3461, 1647, 1219. $^1$H-NMR (CDCl$_3$): δ=5.75 (s, 2), 2.44 (m, 4), 1.64 (m, 4), 1.29 (m, 24), 0.88 (t, 6). $^{13}$C-NMR (CDCl$_3$): 172.77, 70.23, 33.80, 32.07, 29.62, 29.48, 29.40, 29.16, 24.84, 22.88, 14.30. [M+Na]$^+_{theo}$=481.2, GC-MS: [M+Na]$^+_{calc}$=481.6.

Compounds 7a and 7b were prepared in the same manner as the previously synthesized 7c (Djordjevic, et al., J Bioact Compat Pol 2008, 23 (6), 532-551), using (6a or 6b) (1.06 g, 0.19 mmol), N-hydroxysuccinimide (NHS) (0.09 g, 0.77 mmol), and DCC (1M in DCM) (0.31 mL).

Compound 7a: T8P5

White powder (0.92 g, 85%). 1H NMR (CDCl3): δ=0.86 (t, 6), 1.26 (m, 32), 1.60 (b, 4), 2.39 (b, 4), 2.90 (s, 4), 3.41 (m, ~400), 5.66 (s, 2); Mw=5.5 kDa; PDI=1.07.

Compound 7b: T10P5

White powder (0.92 g, 85%). 1H NMR (CDCl3): δ=0.86 (t, 6), 1.26 (m, 32), 1.60 (b, 4), 2.39 (b, 4), 2.90 (s, 4), 3.41 (m, ~400), 5.66 (s, 2); Mw=5.5 kDa; PDI=1.07.

2.4. Critical Micelle Concentration (CMC) Measurements

A solution of pyrene, a fluorescence probe molecule, was made up to a concentration of 5×10$^{-6}$ M in acetone. Samples were prepared by adding 1 mL of pyrene solution to a series of vials and allowing the acetone to evaporate. AMs were dissolved in HPLC grade water and diluted to a series of concentrations from $1\times10^{-3}$ M to $1\times10^{-10}$ M. AM-pyrene solutions (10 mL) were shaken overnight at 37° C. to allow partition of the pyrene into the micelles. The concentration of pyrene in all samples was $5\times10^{-7}$ M. Emission was performed from 300 to 360 nm, with 390 nm as the excitation wavelength. The maximum absorption of pyrene shifted from 332 to 334.5 nm on micelle formation (Astafieva, et al., *Macromolecules* 1993, 26 (26), 7339-7352; Meng, et al., *J Appl Polym Sci* 2009, 114 (4), 2195-2203; Kalyanasundaram, et al., *J Am Chem Soc* 1977, 99 (7), 2039-2044). The ratio of absorption of encapsulated pyrene (334.5 nm) to pyrene in water (332 nm) was plotted as the logarithm of polymer concentrations. The inflection point of the curve was taken as the CMC.

2.5. Isolation and Culture of Human Monocyte Derived Macrophages (hMDMs)

Peripheral blood mononuclear cells (PBMCs) were isolated from human buffy coats and differentiated into macrophages as previously described (Lewis, et al., *Biomaterials* 2013, 34 (32), 7950-9). After differentiation, macrophages were trypsinized, scraped from flasks and transferred into well plates at 50,000 cells/cm$^2$. Macrophages were allowed to adhere for 24 hours before treatments were administered.

2.6. OxLDL Uptake

To measure AM efficacy at inhibiting oxLDL uptake, hMDMs were incubated with 5 µg/mL oxLDL (1 µg/mL DiO labeled, 4 µg/mL unlabeled) and $10^{-6}$ M AMs in RPMI 1640 for 24 h. Following treatment, hMDMs were removed from plates by vigorous pipetting in cold PBS with 2 mM EDTA, centrifuged and fixed in 1% paraformaldehyde.

Uptake of fluorescently labeled oxLDL (DiO) was quantified using a FACS calibur flow cytometer (BD). A minimum of 10,000 macrophages per sample was collected, and quantified using the geometric mean fluorescence intensity (MFI) of oxLDL fluorescence associated with the hMDMs using FloJo software (Treestar). Results represent the mean of four independent experiments. Data is presented as % oxLDL uptake, which was calculated using the following formula: % oxLDL uptake=100*(MFI of AM containing condition)/(MFI of oxLDL control).

2.7. Foam Cell Formation

To measure foam cell formation, hMDMs were incubated with 50 µg/mL oxLDL and $10^{-5}$ M AMs in RPMI 1640 for 24 h before fixation in 4% paraformaldehyde. Cells were washed with 60% isopropanol, stained with 3 mg/mL Oil Red O in 60% isopropanol for 5 min and counterstained with Hoechst 33342.

Oil Red O stained hMDMs were imaged on a Nikon Eclipse TE2000S using a 40× objective. Epifluorescent images of nuclei were merged with transmitted light images using ImageJ.

2.8. Statistical Analysis

All in vitro experiments were replicated a minimum of three times, using primary cells from distinct donors each time. Results are presented as mean±standard error of the mean (S.E.M.) and data evaluated by one-way ANOVA and post-hoc Tukey's test for comparisons between multiple conditions. A p-value of 0.05 or less was considered statistically significant.

2.9. Molecular Modeling

Molecular modeling calculations were performed on selected ester and ether AM model compounds to evaluate similarities and differences in their conformational preferences. All operations were conducted using the Spartan '08 molecular modeling software suite (version 4.0.0, build 131, Wavefunction, Inc., Irvine Calif.). A total of four structural models were constructed and explored, representing model compounds for the respective ester and ether tartaric acid AM analogues as charge-neutral (—COOH) and anionic (COO$^-$) species. The anionic forms depict the putative states that would exist under physiological pH conditions. In each case the model compound structures were identical to the intact AMs under study, aside from the PEG tail which was truncated to five [—O—CH$_2$—CH$_2$] segments capped by a single [—O—CH$_2$—CH$_3$] group. Given the focus on the differential effects of the ester and ether linkages, these model compounds were considered sufficiently representative for this purpose. Preliminary calculations in which more PEG units were sequentially added to the tail revealed an insignificant impact on the findings, and conversely, limited the number of physically meaningful conformers generated in our conformational searches. Molecular mechanics calculations were carried out on each AM model compound using the Merck Molecular Force Field (MMFF) (Halgren, *J. Comp. Chem.*, 17 (5-6), 490-519 (1996)) in an aqueous environment represented the SM5.4 solvent model (MMF-Faq) (Chambers, et al., *J. Phys. Chem.*, 100: 16385-16398 (1996)). A stochastic search of conformational space was implemented on each molecule using a Monte Carlo (MC) procedure that generated 10,000 independent conformers, from which the equilibrium (lowest energy) conformers were selected for subsequent visual inspection. This MC scheme employed a simulated annealing protocol that biases in favor of low-energy conformers but does not completely exclude high-energy conformers.

3. Results and Discussion

Synthesis of ether-linked AMs was completed in three steps: 1) alkylation of free hydroxyl groups of benzyl tartrate; 2) hydrogenolysis to remove the benzyl groups; and 3) coupling to PEG (FIG. 2). Several experiments were performed to determine the optimal conditions (suitable base and solvent) to accomplish the alkylation step. In the experiments described herein, NaH in DMF gave the desired products in ~11% yield, although complete deprotonation of OH group by the base was confirmed by NMR spectroscopy. This yield can be justified by the low reactivity of the halide due to the steric bulk of the long chain, as compared to ~25% yield if the aliphatic chain contains one halogen on each end and recovery of tartaric acid. Although it was reported that DMAP and TEA work in DCM, only starting material was recovered using these reagents; similar low-yielding results were observed with NaHDMS and LDA. Hydrogenolysis of the benzyl esters was carried out with 10% w/w Pd/C in DCM and was quantitative. Finally, products (5) were obtained after coupling of PEG with DCC. Chemical structures of each compound were confirmed via $^1$H NMR, $^{13}$C NMR and IR spectroscopies, as well as mass spectrometry.

Ester-linked AMs were prepared using two procedures as shown in FIG. 3 (Lewis, et al., *Biomaterials* 2013, 34 (32), 7950-7959). Esterification of the vicinal hydroxyl groups in tartaric acid was done using octanoyl/decanoyl/lauroyl chloride and zinc chloride as catalyst. Afterwards, coupling to PEG using DCC in presence of DPTS as catalyst provided the final product after purification.

Measurements of the hydrodynamic radius, melting temperature ($T_m$), and CMC value assessed the impact of replacing the ester bond by an ether on thermal stability and solution properties, which may influence in vivo stability (Table 1). In both polymer classes, increasing the hydrophobic chain length decreased the hydrodynamic radius. This observation is in accordance with the fact that increasing chain length improves the vander Waal's interactions of hydrophobic chains to align and form micelles with hydrophobic core and hydrophilic shell. Notably, the CMC values of ether analogues were about an order-of-magnitude lower than the ester-linked AMs, indicating better solution stability.

Interestingly, all synthesized AMs showed similar Tm values, which suggests that thermal stability depends on the hydrophilic domain PEG (Tm=63° C.) and is in agreement with previous observations (Abdelhamid, et al., *Polymer*

*chemistry* 2014, 5 (4), 1457-1462). In summary, ether- and ester-based AM analogues showed similar physicochemical properties.

TABLE 1

Physicochemical properties of synthesized ether and ester analogues

|  | Ether analogues | | | Ester analogues | | |
|---|---|---|---|---|---|---|
|  | 5a | 5b | 5c | 7a | 7b | 1 |
| Zeta size (nm) | 22 | 20 | 18 | 23 | 18 | 15 |
| Zeta potential (mV) | 0.4 | −1.8 | −2.1 | −2.8 | −1.8 | −1.9 |
| Tm (° C.) | 54-57 | 54-57 | 55-57 | 54-56 | 52-57 | 55-57 |
| CMC (mol/L) | $5.0 \times 10^{-7}$ | $5.1 \times 10^{-6}$ | $8.9 \times 10^{-6}$ | $6.6 \times 10^{-5}$ | $6.4 \times 10^{-5}$ | $6.5 \times 10^{-5}$ |

Figure 4:
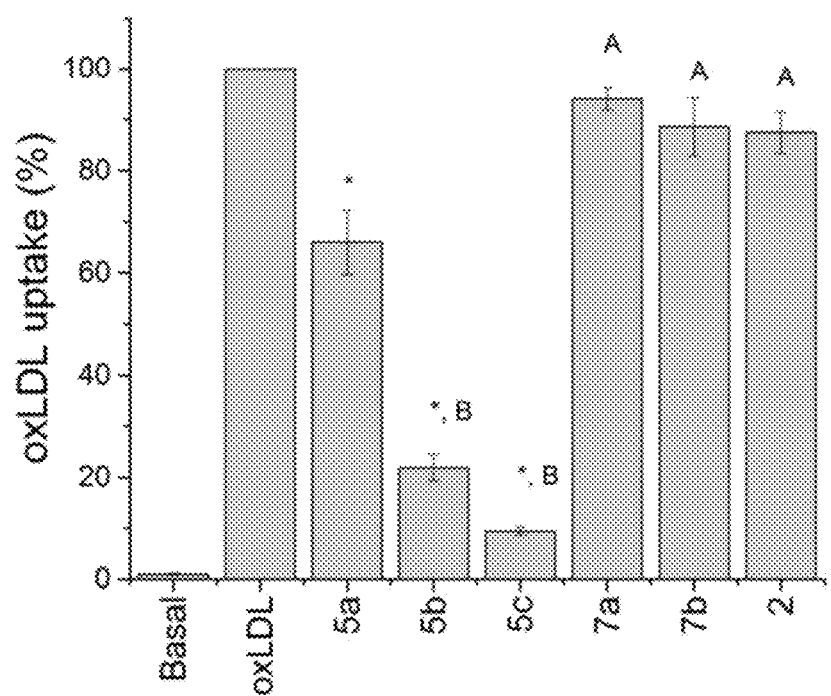
FIG. 4. oxLDL uptake inhibition by tartaric acid-based AMs in hMDMs. The ether-linked AMs had significant reductions in oxLDL uptake, with increased efficacy being directly correlated to longer aliphatic chains. In contrast, the ester structures did not have a significant effect on oxLDL uptake. hMDMs were incubated with 5 μg/mL oxLDL and 10⁻⁶ M AMs in RPMI 1640 for 24 h then analyzed via flow cytometry. * corresponds to p<0.001 relative to oxLDL control, same letter connotes conditions that were not statistically different.

As described above, these new tartaric acid-based AMs with ether or ester bonds were developed to optimize biological activity. As in prior studies, the ability to inhibit oxLDL uptake and the resultant foam cell phenotype was evaluated using human monocyte derived macrophages (hMDMs). Macrophages incubated with ether-linked AMs showed significant reduction in oxLDL uptake as compared to their ester counterparts (FIG. 4). All ester analog-treated conditions were not considered statistically different from the oxLDL alone treated cells. Conversely, all ester-containing AMs structures displayed no significant effect on oxLDL uptake. Additionally, increased inhibitory efficacy directly correlated to hydrophobic chain length. Previous studies found that larger and more hydrophobic sugar moieties resulted in higher levels of oxLDL uptake inhibition (Lewis, et al., *Biomaterials* 2013, 34 (32), 7950-7959). This result is likely the result of tighter binding to the hydrophobic domain of scavenger receptors.

Figure 5:
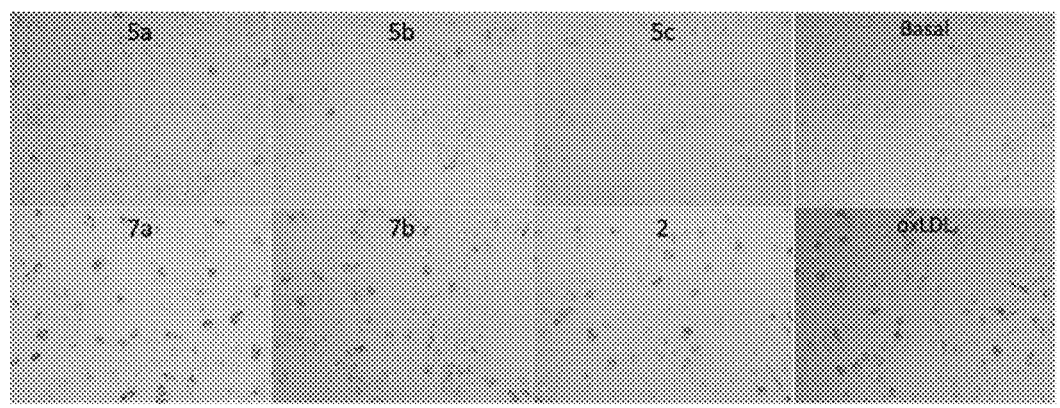
FIG. 5. Foam cell formation in hMDMs. hMDMs were incubated with 50 μg/mL oxLDL and 10⁻⁵ M AMs in RPMI 1640 for 24 h before staining with Oil Red O and Hoechst 33342. The ether-based AMs demonstrated more effective rescued foam cell formation, with the longest alkyl chain (5c) displaying the highest effectiveness.
Figure 6:
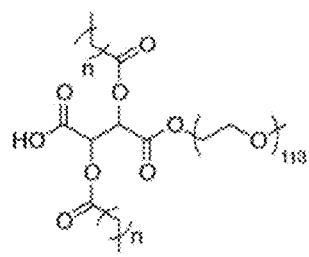
FIG. 6. Certain embodiments of tartaric acid-based AMs with altered connectivity between the sugar backbone and hydrophobic chains as compared to the conventional AM with ester linkages. As shown in this figure, n may be any integer, e.g., between 1 and 20, e.g., between 4 and 14, or e.g., between 6 and 10.
Figure 6:
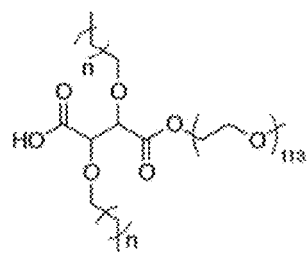
Figure 6:
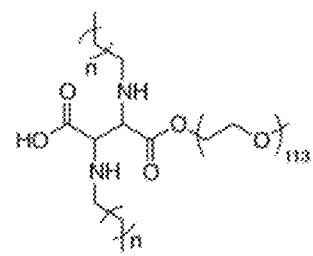
Figure 6:
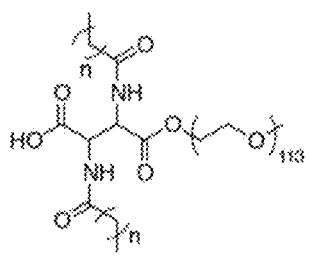
Figure 6:
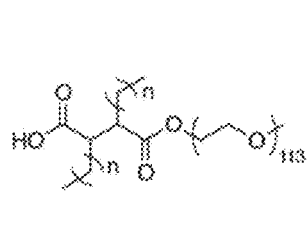
Figure 7:
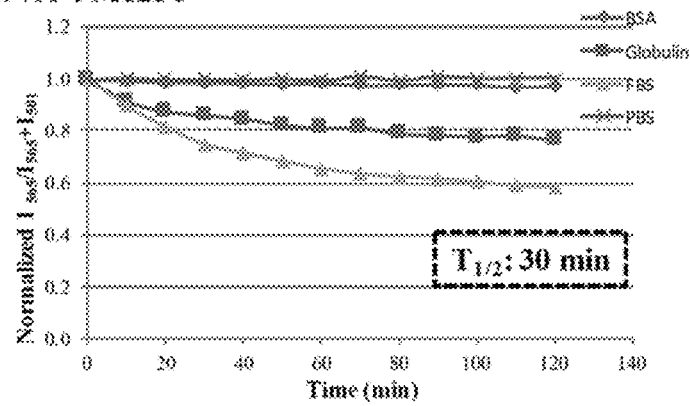
FIGS. 7A-C. Stability of FRET-micelles in the presence of FBS is compared to PBS (control) and each of the major serum proteins. Time traces of the FRET ratio, I565/(I565+I501), normalized to time 0, in solutions of (b) PBS at pH 7.4, (9) R-, β-globulins at 15 mg/mL, (2) γ-globulins at 15 mg/mL. BSA at 45 mg/mL, and 100% FBS (n=3 independent experiments, mean (standard deviation plotted)).
Figure 7:
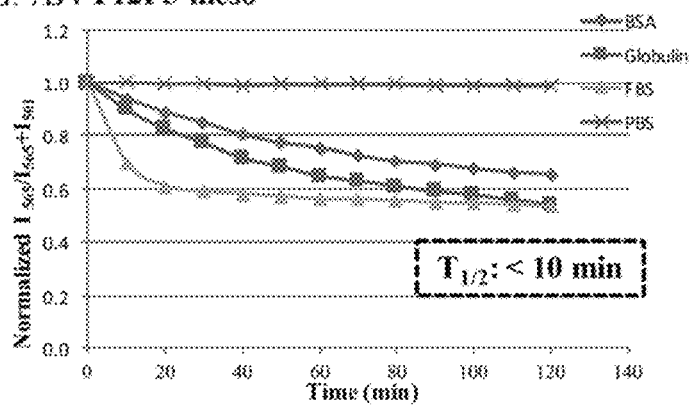
Figure 7:
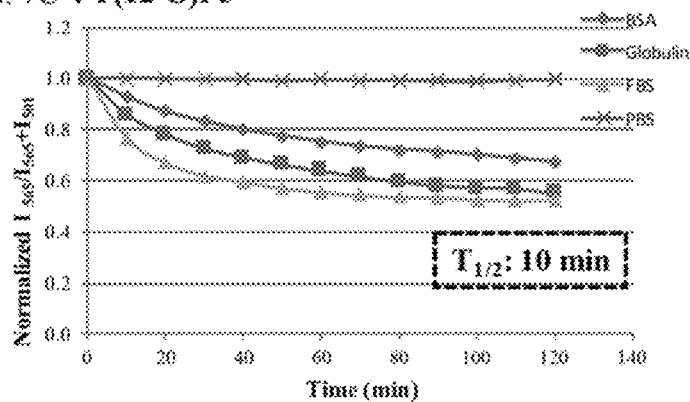

As foam cell formation is the major endpoint event in the atherogenic cascade, the ability to prevent foam cell formation in hMDMs was also examined by blocking the internalization of oxidized lipids. Similar to oxLDL uptake studies, ether-linked AMs showed remarkable inhibition of lipid accumulation and were far more efficacious than ester analogues (FIG. 5). Cells treated with ether-linked AM structures had minimal formation of intracellular lipid droplets and maintained a basal morphology. Ester AM treated conditions displayed a morphology similar to oxLDL-only treated cells, including large lipid droplets and an enlarged phenotype. These results confirm that structural changes of the hydrophobic domain immensely impact the binding affinity and minor modifications can improve the biological activity.

In comparing the efficacy of the ether-linked AMs to the most potent, previously developed AMs, similar levels of inhibitory activity were seen. Despite a smaller hydrophobic domain, the ether-linked AM 5c was able to reduce oxLDL uptake by ~90%, compared to an ~85% reduction in with the previously developed AM, $^{[-1]}M_{12}P_{5k}$ (De Meyer, 1997). Although hydrophobicity was previously shown to play a large role in determining AM efficacy, this study indicates that other factors can influence bioactivity.

To understand the reason behind the remarkable difference in bioactivity between the ether and ester analogues, a previously developed molecular modeling framework was adapted to computationally screen biomaterials with anti-atherosclerotic properties (Lewis, et al., *Biomaterials* 2013, 34 (32), 7950-9). The molecular modeling studies reveal striking differences between the ester and ether tartaric acid AM analogues in terms of their conformational features and overall molecular architectures. For the ether analogue, the two C12-alkyl side chains adopt a near parallel alignment and are pointed away from the PEG tail. For the corresponding ester, in sharp contrast, the alkyl side chains adopt an oblique orientation with an intersection angle of approximately 40°. The better alignment of side chains for the ether case may be expected to provide an energetically more favorable interaction with the hydrophobic surface of the SR. This conformational disparity between the ether and ester analogues can be traced to differences in rotational flexibility between their corresponding —C—O—C— and —C(C═O)—O—C— linkers. The ether link is relatively small and quite flexible which allows the two side chains to adopt a compact parallel alignment. In contrast, the ester link is rotationally less flexible due to the steric crowding between the adjacent ester groups and the bias toward an antiparallel orientation of their dipoles that directs the alkyl side chains in eccentric directions. The fairly modest (32%) difference in dipole moment between dimethyl ether (1.3 D) and methyl acetate (1.72 D) would suggest that steric crowding of the adjacent ester linkers may play a significant role.

Inspection of the entire AM structures in their equilibrium conformations offers a glimpse into the configurations in aqueous solution as may exist under physiological solutions. In both the ether and ester cases, a strong hydrophilic interaction has formed between the —COOH head group and the PEG tail at either ends of the tartaric acid sugar. Specifically, the OH group of the —COOH engages in a hydrogen bond (O—H . . . O distance 2.7 Å) with backbone —O— atoms in the PEG unit. This interaction of the hydrophilic —COOH and PEG moieties coincides with a dramatic bowing of the entire molecule such that the amphiphilic nature of the AM is immediately apparent. This amphiphile effectively partitions the two lipophilic alkyl side chains and the hydrophilic —COOH . . . PEG dyad and orients them in opposite directions. Compared with the ester, the ether analogue presents the more streamlined amphiphilic molecule which may facilitate its biological activity. It also suggests that the ether is more amenable than the ester to micelle formation, i.e., the ether analogue would be predicted to possess a lower CMC.

The equilibrium conformations obtained from the MC search for the anionic forms of the ester and ether AM analogues closely resemble their arrangement in the corresponding neutral forms. Despite the absence of the COOH•••PEH hydrogen bond, it appears that the solvated COO⁻ anion serves very much in the same capacity as the hydrogen bonding OH of the COOH head group to "seed" formation of the hydrophilic cluster with the PEG unit.

A few points are notable about the present molecular modeling simulations. First, the calculations employed an implicit (SM5.4) aqueous solvent model. These calculations may be repeated in an aqueous bath using explicit water ($H_2O$) molecules. Second, the present findings represent the behavior of a single model AM structure; other molecular simulation methods and a multicomponent system, such as those considered in Lewis, et al., *Biomaterials* 2013, 34 (32), 7950-9 may be performed. Finally, results from the present calculations demonstrate that seemingly minor changes in the structures of these AMs can translate to significant alterations in their physicochemical properties and biological activity.

EXAMPLE 2

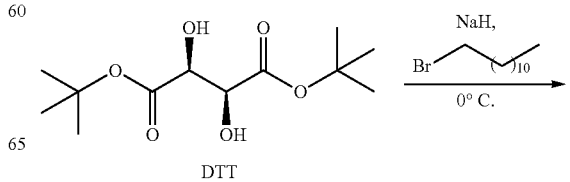

DTT

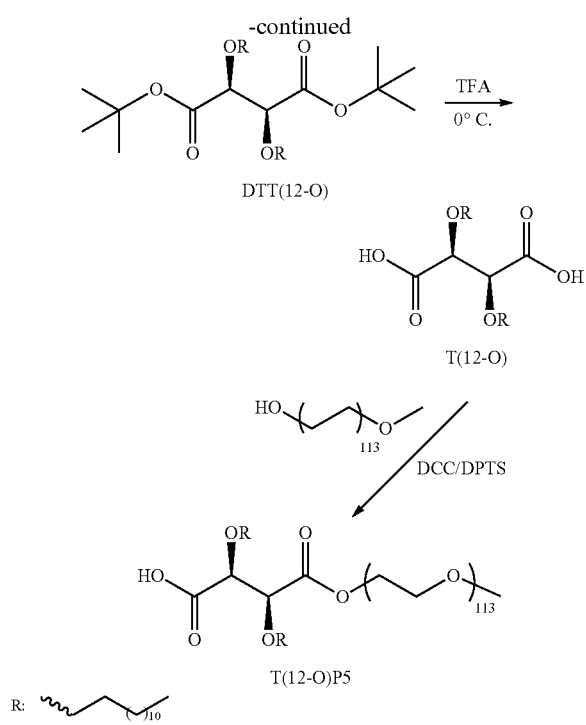

Synthesis of T(12-O)P5

DTT(12-O). Di-tert-butyl L-tartrate (DTT, 500 mg, 1.91 mmol) was dissolved in 15 mL anhydrous DMF and cooled to 0° C. using an ice bath. Sodium hydride (NaH, 160 mg, 4.00 mmol) was added subsequently and the reaction was stirred for 20 min. Bromododecane (1.04 mL, 4.19 mmol) was added dropwise to the reaction via syringe pump. The reaction progress was monitored by silica gel thin layer chromatography (Hexane: Ethyl acetate=85:15). After Di-tert-butyl L-tartrate was completely consumed, the reaction was allowed to stir for an additional 2 h before stopped. The reaction was quenched with saturated ammonium chloride ($NH_4Cl$) solution and extracted with ethyl acetate (3×20 mL). Organic layers were combined, washed with brine (1×60 mL), and dried over magnesium sulfate ($MgSO_4$) before solvent was removed in vacuo. DTT(12-O) was purified on silica gel via column chromatography using a hexane: ethyl acetate gradient (100:0 to 98:2). Yield: 548 mg, 48% (clear, colorless oil). $^1$H-NMR (400 MHz, $CDCl_3$): 4.16 (s, 2H), 3.72 (m, 2H), 130 (m, 2H), 1.60 (m, 4H), 1.49 (s, 18H), 1.24 (b, 36H), 0.88 (t, 6H). $^{13}$C-NMR (500 MHz, $CDCl_3$): 169.18, 81.93, 80.69, 72.68, 32.15, 29.87, 29.57, 28.37, 26.25, 22.91, 14.34. IR ($cm^{-1}$, thin film from $CHCl_3$): 1751 (C=O, ester), 1258 (C—O, ether). ESI-MS m/z: 621.4 $[M+Na]^+$.

T(12-O): DTT(12-O) (247 mg, 0.412 mmol) was dissolved in dichloromethane (DCM) under argon and cooled to 0° C. using an ice bath. Trifluoroacetic acid (TFA, 1.26 mL, 16.48 mmol) was then added dropwise via syringe and the reaction was stirred overnight. The reaction mixture was concentrated in vacuo and the pure product was precipitated in chilled hexane and collected via vacuum filtration. Yield: 182 mg, 91% (white powder). $^1$H-NMR (400 MHz, $CDCl_3$): 4.38 (s, 2H), 3.69 (m, 2H), 3.53 (m, 2H), 1.60 (m, 4H), 1.25 (b, 36H), 0.88 (t, 6H). $^{13}$C-NMR (500 MHz, $CDCl_3$): 172.49, 79.40, 73.64, 34.20, 31.90, 29.63, 29.61, 29.57, 29.49, 29.35, 29.33, 29.27, 25.72, 22.67, 14.10. IR ($cm^{-1}$, thin film from $CHCl_3$): 3500-3300 (OH, COOH), 1644 (C=O, COOH), 1265 (C—O, ether). ESI-MS m/z: 485.7 $[M-H]^-$.

T(12-O)P5. Following a previously published method, T(12-O) (136 mg, 0.28 mmol) and DPTS (24.5 mg, 0.25 mmol) were dissolved in 3 mL anhydrous DCM and 0.2 mL DMF. This solution was added to PEG (467 mg, 0.09 mmol). Once PEG was completely dissolved, N,N'-dicyclohexylcarbodiimide (DCC, 1 M in DCM, 0.29 mmol) was added dropwise via syringe and the reaction was stirred under argon. After 48 h, the reaction mixture was cooled at −20° C. DCC side product (dicyclohexylurea) was precipitated and removed by vacuum filtration. The filtrate was washed with 0.1 N HCl (1×25 mL) and brine (2×25 mL). The combined organic layer was dried over $MgSO_4$, and concentrated in vacuo. The crude product was purified by precipitation into chilled diethyl ether and isolated via centrifugation. Yield: 356 mg, 72% (white powder). $^1$H-NMR (400 MHz, $CDCl_3$): 4.33 (b, 2H), 3.64 (b, ~500H), 1.64 (m, 4H), 1.25 (b, 36H), 0.88 (t, 6H). $M_w$, 5.2 kDa; PDI, 1.1.

EXAMPLE 3

Degradation Stability

Metabolic instability, particularly susceptibility to enzyme-catalyzed degradation, has long been considered a primary factor responsible for failure of drug candidates translating from in vitro work to clinical phase. Due to the presence of hydrolysable ester linkages in AMs and abundance of lipase in blood, it's important to take influence of lipase-mediated degradation on efficacy into consideration. Previously, the chemical composition change of AMs was examined upon incubation with lipase solution over 24 h via $^1$H-NMR. Herein, it is further studied how AM degradation alter their respective bioactivity in vitro by treating HMDMs with degraded AMs reconstituted in PBS buffer at predetermined concentrations under serum-free conditions. Degraded AMs were extracted from degradation media with DCM and redissolved in PBS, ascertaining the complete removal of water soluble lipase, which may influence subsequent oxLDL uptake study.

Figure 8:
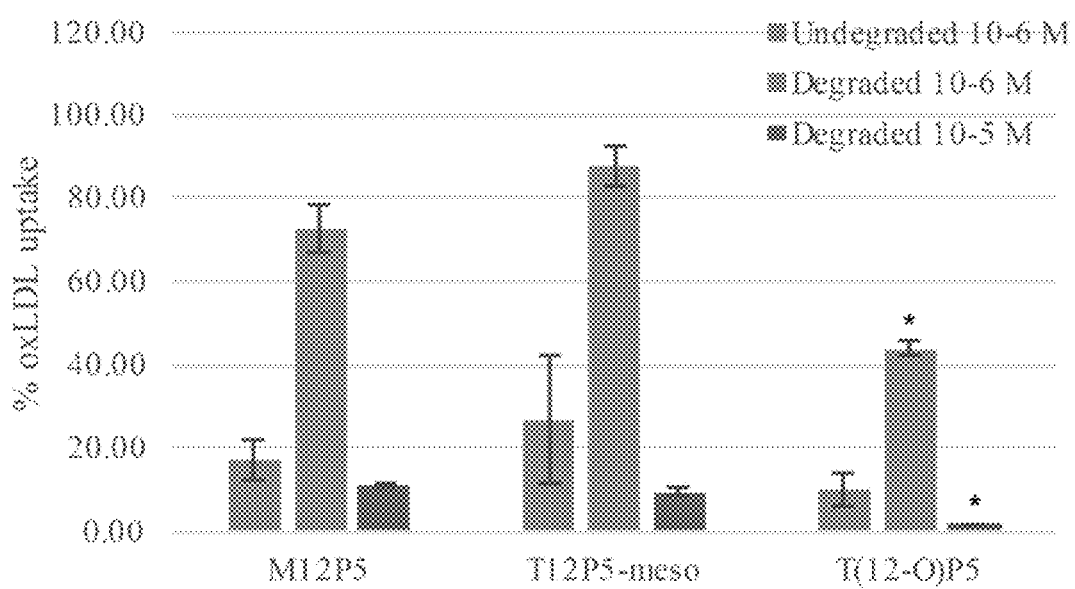
FIG. 8. Illustrates data from Example 3, with the first column in each set representing 'Undegraded 10-6 M', the second 'Degraded 10-6 M' and the third 'Degraded 10-5 M'.

As shown in FIG. 8, degraded AMs were approximately 3-4 fold less efficient in reducing oxLDL accumulation compared to undegraded AMs at $10^{-6}$ M. As expected, lipase-catalyzed ester degradation significantly reduced effective AM concentrations or AM bioavailability, leading to compromised efficacy. In fact, minimum residual bioactivity was detected as oxLDL uptake as high as 73% and 88% were observed for ester-linked AMs M12P5 and T12P5-meso, respectively. It is noteworthy that ether-linked AM T(12-O)P5 was still able to retain an oxLDL uptake level as low as 44% after 24 h lipase incubation, which was significant better than when treated with ester-linked AMs. This phenomenon likely resulted from enhanced degradation stability conferred by ether linkage as previously discussed. The result further validated and confirmed the necessity of improving enzymatic degradation stability for enhanced bioactivity in vivo. An evident concentration-dependent effect of AMs was once more observed. When administered at $10^{-5}$ M, all AMs remarkably repressed the oxLDL uptake, particularly with T(12-O)P5 to a basal level.

CONCLUSIONS

Novel AMs were designed and synthesized to investigate the impact of functional group linking the hydrophobic chain to sugar on biological activity and physicochemical properties. Similar physicochemical properties were observed for both classes, however, ether-linked AMs displayed significantly higher ability to inhibit oxLDL uptake and foam cell formation; two key steps in atherosclerosis. Furthermore, molecular modeling studies suggest that the higher activity can be attributed to the increased flexibility of the ether linkage, which facilitates hydrogen-bonding of the sugar carboxylate with the hydrophilic PEG tail. Data generated in this study provide valuable insights regarding the design of potent AMs for the treatment of cardiovascular disease.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. A compound of formula (I):

A-X—Y—Z—R$_1$           (I), or a salt thereof, wherein:
   A is a carboxy group;
   X is a straight chain or branched chain aliphatic group containing from 2 carbons to about 10 carbons, wherein the aliphatic group is substituted with 1 or more groups independently selected from —OR$^a$, and —NR$^b$R$^c$; wherein R$^a$ is independently selected from a —(C$_1$-C$_{20}$)alkyl, —(C$_2$-C$_{20}$)alkenyl and —(C$_2$-C$_{20}$)alkynyl; wherein R$^b$ is independently H or (C$_1$-C$_6$)alkyl; and wherein R$^c$ is independently selected from a —(C$_1$-C$_{20}$)alkyl, —(C$_2$-C$_{20}$)alkenyl and —(C$_2$-C$_{20}$)alkynyl;
   Y is —C(=O);
   Z is O or NH; and
   R$_1$ is a poly(alkylene oxide) having between about 2 and about 150 repeating units.

2. The compound of claim 1, wherein the aliphatic group is substituted with 1 or more —OR$^a$ groups.

3. The compound of claim 1, wherein the aliphatic group is substituted with 1 or more —NR$^b$R$^c$ groups.

4. The compound of claim 1, wherein Z is O.

5. The compound of claim 1, wherein R$_1$ is:

wherein n is about 2 to about 150.

6. The compound of claim 1, selected from:

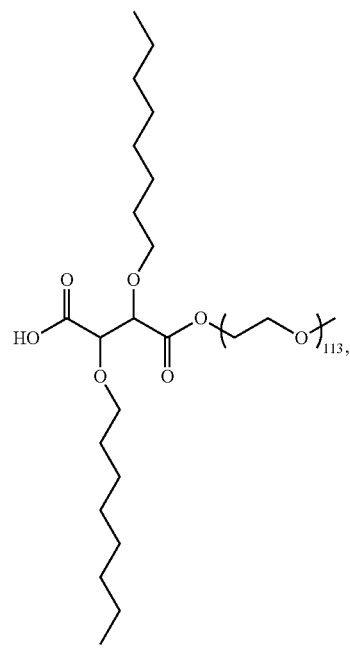

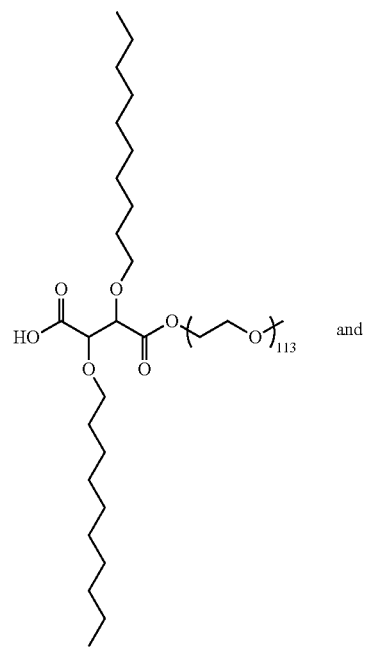

and

-continued

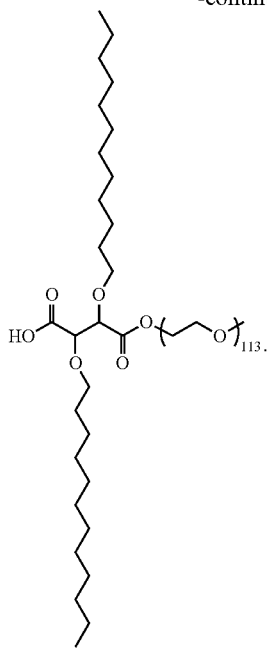

7. A composition comprising a plurality of compounds of formula (I) as described in claim 1, in a solvent.

8. An aggregate structure comprising a plurality of compounds of formula (I), as described in claim 1, and a solvent.

9. A method for preparing an aggregate structure, comprising combining a plurality of compounds of formula (I), as described in claim 1, in a solvent; and allowing them to form the aggregate structure.

10. An encapsulate comprising a molecule surrounded or partially surrounded by a plurality of compounds of formula (I), as described in claim 1.

11. A method for preparing an encapsulate, comprising combining a) a plurality of compounds of formula (I), as described in claim 1; b) a molecule; and c) a solvent; and allowing the compounds of formula (I) to aggregate around the molecule, to provide the encapsulate.

12. A pharmaceutical composition comprising a compound of formula (I), as described in claim 1, or a pharmaceutically acceptable salt thereof, and a pharmaceutically acceptable carrier.

13. A pharmaceutical composition comprising an encapsulate, as described in claim 10, and a pharmaceutically acceptable carrier.

14. A method for inhibiting oxLDL uptake by a cell, comprising contacting the cell in vitro or in vivo with a compound of formula (I), as described in claim 1, or a pharmaceutically acceptable salt thereof.

15. A method of preventing foam cell formation and/or for inhibiting atherosclerosis or atherosclerotic development in a mammal, comprising administering to the mammal an effective amount of a compound of formula (I), as described in claim 1, or a pharmaceutically acceptable salt thereof.

16. A method for preparing a compound of formula (I) as described in claim 1:

$$A\text{-}X\text{—}Y\text{—}Z\text{—}R_1 \quad (I),$$

wherein Z is O, comprising esterifying a corresponding compound of formula (Ia):

$$A\text{-}X\text{—}Y\text{—}Z\text{—}R_{1'} \quad (Ia)$$

wherein $R_{1'}$ is H with a hydroxyl polyether residue to provide the compound of formula (I).

17. The compound of claim 1, wherein X is a straight chain or branched chain aliphatic group containing from 2 carbons to 4 carbons, wherein the aliphatic group is substituted with 1 or more —$OR^a$ groups.

18. The compound of claim 1, wherein $R^a$ is —($C_6$-$C_{14}$) alkyl.

19. The compound of claim 5, wherein n is about 110 to about 120.

20. The compound of claim 1, which is:

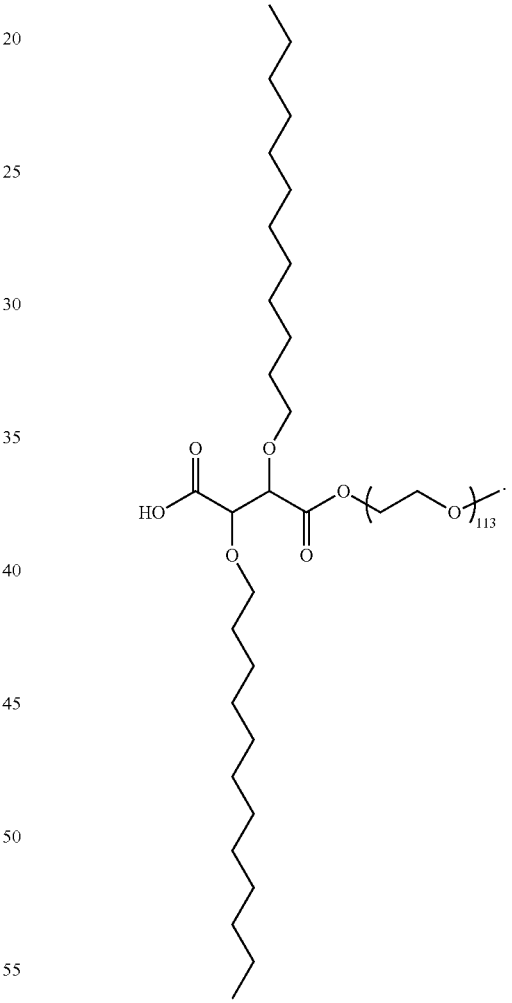

* * * * *